(12) United States Patent
De Santis et al.

(10) Patent No.: US 7,989,171 B2
(45) Date of Patent: Aug. 2, 2011

(54) ANTI-HUMAN TENASCIN MONOCLONAL ANTIBODY

(75) Inventors: Rita De Santis, Pomezia (IT); Angela Pelliccia, Rome (IT); Giovanna Palombo, Naples (IT); Paolo Carminati, Milan (IT)

(73) Assignee: Tecnogen S.C.P.A., Verna (CE) (IT)

( * ) Notice: Subject to any disclaimer, the term of this patent is extended or adjusted under 35 U.S.C. 154(b) by 1230 days.

(21) Appl. No.: 10/590,936

(22) PCT Filed: Feb. 16, 2005

(86) PCT No.: PCT/IT2005/000078
§ 371 (c)(1),
(2), (4) Date: Aug. 28, 2006

(87) PCT Pub. No.: WO2005/082938
PCT Pub. Date: Sep. 9, 2005

(65) Prior Publication Data
US 2010/0297003 A1   Nov. 25, 2010

(30) Foreign Application Priority Data

Feb. 27, 2004   (IT) .............................. RM2004A0105

(51) Int. Cl.
*G01N 33/53* (2006.01)
*C12P 21/02* (2006.01)
*C07K 16/00* (2006.01)

(52) U.S. Cl. .................. 435/7.1; 530/387.1; 530/391.1; 530/387.7; 435/810; 435/70.2

(58) Field of Classification Search .................. None
See application file for complete search history.

(56) References Cited

U.S. PATENT DOCUMENTS 6,335,014 B1   1/2002   Kusakabe 7,390,828 B2 *   6/2008   Paganelli et al. ............ 514/387
7,425,317 B2 *   9/2008   De Santis et al. ............ 424/1.49

FOREIGN PATENT DOCUMENTS

| JP | 2002-234900 | 8/2002 |
| WO | 02/066075 | 8/2002 |
| WO | 03/072608 A | 9/2003 |
| WO | 03/075960 | 9/2003 |

OTHER PUBLICATIONS

De Santis et al. Additivity of two anti-tenascin monoclonal antibodies for pre-targeted antibody guided radioimmunotherapy (PAGRIT). Cancer Biotherapy & Radiopharmaceuticals. Aug. 2004, 19(4): 512-541., Abstract #26.*
International Search Report of PCT/IT2005/000078, mailed Oct. 26, 2005.
Siri et al., "Human Tenascin: Primary Structure, Pre-MRNA Splicing Patterns and Localization of the Epitopes Recognized by Two Monoclonal Antibodies", Nucleic Acids Research, vol. 19, No. 5, 1991, pp. 525-531, XP000919423.
Balza et al., "Production and Characterization of monoclonal antibodies specific for different epitopes of human tenascin", FEBS Letters, vol. 332, No. 1-2, 1993, pp. 39-43, XP002349140.
Paganelli et al., "Antibody-Guided Three-Step Therapy for High Grade Glioma With Yttrium-90 Biotin", European Journal of Nuclear Medicine, vol. 26, No. 4, Apr. 1999, pp. 348-357, XP008019281.

* cited by examiner

*Primary Examiner* — Maher Haddad
(74) *Attorney, Agent, or Firm* — Lucas & Mercanti LLP

(57) ABSTRACT

An anti-human tenascin monoclonal antibody is described, whose light and heavy chain variable region sequences are SEQ ID 1 and SEQ ID 2, respectively, its proteolytic fragments capable of binding to an antigenic epitope within the region $A_{(1-4)}$-D of human tenascin, its recombinant derivatives, its conjugates and its similar functional analogues capable of binding to an antigenic epitope within the $A_{(1-4)}$-D region of human tenascin.

19 Claims, 21 Drawing Sheets

Schematic representation of human tenascin-C and of the strategy followed for the generation of BC2-like antibodies SDS-PAGE and Western Blot analysis of ST2485 antibody, in reducing (b, d) and non-reducing (a, c) conditions.

SDS-PAGE a)

b)

Western Blot c)

d)

M: molecular weight standards

ST2485 antibody digestion with Flavobacterium Peptide-N-glycosidase enzyme (PNGase F).

1: Molecular weight marker

2: Non-digested ST2485

3: PNGaseF-digested ST2485

BC-2 and ST2485 antitenascin antibodies hydroxyapatite chromatography.

ST2485 antitenascin antibody Western Blot Analysis

1: Tenascin-C

2: Tn A$_{(1-4)}$-D Fragment

3: Tenascin EGF-like region recombinant fragment, containing the epitope recognized by BC-4 antibody.

MW: molecular weight standards

Competitive ELISA test between ST2485 and BC-2 for antigen binding.

a)

b)

Immunoreactivity of ST2485 antibody in comparison with BC-2, on tenascin C (a) and on Tn $A_{(1-4)}$-D fragment (b).

Immunoreactivity of ST2485 and BC-2 biotinylated and non-biotinylated antibodies, on tenascin-C (a) and on Tn $A_{(1-4)}$-D fragment (b).

a)

b)

Cross-reactivity of ST2485 antibody with murine tenascin.

Biotinylated ST2485 and BC-2 biodistribution in human tenascin-expressing tumor-transplanted nude mice. The antibody amount is expressed as percent of the injected dose per tissue gram (% I.D./gr).

Biotinylated ST2485 and BC-2 biodistribution in nude mice: tumor/non tumor ratio.

Interference (a) and additivity (b) ST2485 and ST2146 antitenascin antibodies *in vitro* evaluation by ELISA test.

a) Interference b) Additivity

Antibodies ST2485 and ST2146 tenascin binding *in vitro* additivity by BIACore a)

b)

c)

d)

Schematic representation of *in vivo* additivity study in animal model

ST2485 e ST2146 antibodies additivity in animal model; tumor seat localization.

Figure 17

SEQ ID No. 2 sequence of ST2485 kappa light chain variable region (VL).
*Signal peptide*
*ATGGATTTTCAAGTGCAGATTTTCAGCTTCCTGCTAATCAGTGCTTCAGTCATAATGTCCAGAGGA*CAAA
*Met Asp Phe Gln Val Gln Ile Phe Ser Phe Leu Leu Ile Ser Ala Ser Val Ile Met Ser Arg Gly* Gln TTGTTCTCTCCCAGTCTCCAGCAATCCTGTCTGCATCTCCAGGGGAGAAGGTCACAATGACTTGC
Ile Val Leu Ser Gln Ser Pro Ala Ile Leu Ser Ala Ser Pro Gly Glu Lys Val Thr Met Thr Cys ↓ N-glycosylation
CDR1
AGGGCCAACTCAAGTGTACGTTTCATGCACTGGTACCAGCAGAAGCCAGGATCCTCCCCCAAACC
Arg Ala Asn Ser Ser Val Arg Phe Met His Trp Tyr Gln Gln Lys Pro Gly Ser Ser Pro Lys

CDR2
CTGGATTTATGCCACATCCAACCTGGCTTCTGGAGTCCCTGCTCGCTTCAGTGGCAGTGGGTCTGG
Pro Trp Ile Tyr Ala Thr Ser Asn Leu Ala Ser Gly Val Pro Ala Arg Phe Ser Gly Ser Gly

CDR3
GACCTCTTATTCTGTCACAATCAGCAGAGTGGAGGCTGAAGATGCTGCCACTTATTACTGCCAGC
Ser Gly Thr Ser Tyr Ser Val Thr Ile Ser Arg Val Glu Ala Glu Asp Ala Ala Thr Tyr Tyr Cys Gln

AGTGGAGTAGTAATTCACCCAGGACGTTCGGTGGAGGCACCAAGGTGGAAATCAGACGGGCT
Gln Trp Ser Ser Asn Ser Pro Arg Thr Phe Gly Gly Gly Thr Lys Val Glu Ile Arg Arg Ala

Figure 18

SEQ ID No. 4 sequence of ST2485 gamma heavy chain variable region (VH)

*Signal peptide*
<u>ATGGGATGGAGCTGGATCTTTCTCTTCCTCCTGTCAGGAACTGCAGGTGTCCACTCT</u>GAGGTCCAGCTG
<u>Met Gly Trp Ser Trp Ile Phe Leu Phe Leu Leu Ser Gly Thr Ala Gly Val His Ser</u> Glu Val Gln Leu CAACAGTCTGGACCTGAGCTGGTGAAGCCTGGAGCTTCAATGAAGATTTCCTGCAAGGCTTCTGG
Gln Gln Ser Gly Pro Glu Leu Val Lys Pro Gly Ala Ser Met Lys Ile Ser Cys Lys Ala Ser CDR1
TTACTCATTCACTGGTTACACCATGAACTGGGTGAAGCAGAGCCATGGAAAGAACCTTGAATGGA
Gly Tyr Ser Phe Thr Gly Tyr Thr Met Asn Trp Val Lys Gln Ser His Gly Lys Asn Leu Glu Trp CDR2
TTGGACTTATTAATCCTCACAATGGTGGTACTACCTACAACCAGAAGTTCAAGGGCAAGGCCACA
Ile Gly Leu Ile Asn Pro His Asn Gly Gly Thr Thr Tyr Asn Gln Lys Phe Lys Gly Lys Ala Thr TTAACTGTAGACAAGTCATCCAACACAGCCTACATGGAGCTCCTCAGTCTGACATCTGAGGACTC
Leu Thr Val Asp Lys Ser Ser Asn Thr Ala Tyr Met Glu Leu Leu Ser Leu Thr Ser Glu Asp CDR3
TGCAGTCTATTACTGTACAAGACCCGGGGGTTACTACTGGTTCTTCGATGTCTGGGGCGCAGGGA
Ser Ala Val Tyr Tyr Cys Thr Arg Pro Gly Gly Tyr Tyr Trp Phe Phe Asp Val Trp Gly Ala Gly CCACGGTCACCGTCTCCTCA
Thr Thr Val Thr Val Ser Ser

ANTI-HUMAN TENASCIN MONOCLONAL ANTIBODY

This application is the US national phase of international application PCT/IT2005/000078, filed 16 Feb. 2005, which designated the U.S. and claims priority of IT RM2004A000105, filed 27 Feb. 2004, the entire contents of each of which are hereby incorporated by reference.

The present invention relates to anti-human tenascin monoclonal antibodies, methods and materials for obtaining them, the use of said antibodies in diagnostic and treatment procedures for tumours expressing tenascin and materials containing said antibodies suitable for use in the medical field.

BACKGROUND TO THE INVENTION

The specificity of tumour therapy often constitutes a limiting factor in determining the success of the treatment. In fact, the onset of toxic effects and the reduced tolerability of a number of anticancer agents limit their use and the quality of life of the patients.

The reduction of toxicity is directly linked to the selectivity of the treatment for cancer cells alone. Monoclonal antibodies are the ideal instrument for specifically localising the tumour and, when combined with the avidin/biotin amplification system, constitute an extremely potent method for directing active molecules to the tumour site.

Tenascin is a molecule of the extracellular matrix, expressed during embryogenesis and in adult tissues during the processes of scar formation and tumour development, as well as in newly formed blood vessels. Tenascin is virtually absent in normal adult tissues, whereas it is expressed in the stroma of many solid tumours such as gliomas (Burdon, et al., Cancer. Res., 43:2796-2805, 1983), carcinomas of the breast (Chiquet-Ehrismann, et al., 1986), lung (Natali, et al., Intl. J. Cancer, 54: 56-68, 1989), fibrosarcomas and squamous-cell carcinomas (Ramos, D. M. et al., Intl. J. Cancer, 75:680-687, 1998). Tenascin is expressed in glioma, but not in the corresponding normal brain tissue. For an in-depth discussion of tenascin, the reader is referred to WO 92/04464, Wistar and related references.

On the basis of EP 0 496 074, G. Paganelli et al. have developed a method called "three-step pre-targeting" for the systemic and locoregional treatment of tumours, the results of which are reported in: Cremonesi, M., et al., Eur. J. Nucl. Med., 26 (2):110-120, 1999; Paganelli, G., et al., Eur. J. Nucl. Med., 26 (4):348-357, 1999; Paganelli, G., et al., Cancer Biother. & Radiopharin., 16 (3):227-235, 2001; Grana, C., et al., Br. J. Cancer, 86:207-212, 2001.

Other references for this type of cancer treatment are: WO 94/04702, and U.S. Pat. No. 5,578,287.

Three-step pre-targeting treatment, also known sotto by the trade-mark PAGRIT®, is based on the sequential intravenous administration of a biotinylated anti-tenascin monoclonal antibody, streptavidin and $^{90}$Y-biotin, with administrations of avidin and biotinylated albumin prior to the streptavidin and $^{90}$Y-biotin, respectively ("chase" step), to reduce the circulating levels of the antibody and of streptavidin. The selectivity of the 3-step pre-targeting method is due to the use of the anti-tenascin monoclonal antibody. The targeting of extracellular matrix molecules presents the advantage, compared to targeting aimed at cell surface antigens, of not being affected by modulation of antigen expression by the tumour cell itself. The doses, administration times and "chases" of the pre-targeting treatment have been established for the purposes of obtaining optimal tumour to non-tumour biodistribution ratios.

The results obtained in 48 patients suffering from glioblastoma (GBM) or anaplastic astrocytoma (AA), entered into a study by Paganelli (Paganelli, G., et al., Eur. J. Nucl. Med., 26 (4):348-357, 1999), have demonstrated a substantial lack of toxicity, except for a number of cases of allergic reaction to streptavidin, and preliminary efficacy of the treatment. In fact, 2 months after the end of the treatment, 25% of the patients showed a reduction of the tumour mass (Complete Response=6%, Partial Response=11%, Minor Response=8%), and 52% of patients remained stable, with an overall response rate of 77%. In a number of these patients, whose life expectancies were below six months, the response to treatment persisted for more than one year.

The role of the biotinylated anti-tenascin antibody is to localise in the tumour and mediate, via the biotinylated molecule, the accumulation of avidin and subsequently of $^{90}$Y-biotin, directing the radioisotopes directly into the interior of the tumour. Anti-tenascin antibodies are already the object of patents and patent applications: U.S. Pat. No. 5,624,659, Duke University; JP 2219590, Rikagaku; WO 92/04464, Wistar; and WO 03/072608, Sigma-Tau.

One particular anti-tenascin antibody is described in: Siri, A., et al, Nucl. Acid Res., 19(3):525-531, 1991; Balza, E., et al, FEBS 332:39-43, 1993; and its use for therapeutic purposes is described in: Riva, P., et al., Acta Oncol. 38(3):351-9, 1999; Riva, P., et al, Cancer, 80 (12): 2733-42; 1997; Riva, P., et al., Int. J. Cancer, 5:7-13, 1992.

The clone used for the generation of said antibody in the above-cited studies is called BC-2. The applicant has demonstrated that the clone BC-2 is not suitable for industrial development, in that it produces an additional non-functional light chain (probably deriving from the parent myeloma line) whose level of expression increases during development of the production process on a large scale, preventing industrial-scale purification of the antibody.

There is therefore a perceived need for an anti-tenascin monoclonal antibody that can be produced on an industrial scale at the purity levels required for pharmaceutical use.

The previous patent application WO 03/072608, filed in the name of Sigma Tau Industrie Farmaceutiche Riunite S.p.A., describes the generation of the anti-tenascin antibody ST2146, without the additional non-functional light chain, capable of recognising an antigenic epitope shared with antibody BC-4, also contaminated by a non-functional light chain.

Antibody ST2485, the object of the present invention, recognises an epitope partly shared with that of BC-2, and therefore located in the same protein region. This region is greatly expressed in various tumour tissues. It is therefore important to have a homogeneous monoclonal antibody which is specific for this region, to be used for cancer diagnosis or targeting.

Moreover, the present invention demonstrates that antibody ST2485 presents the advantage of binding to tenascin in addition to antibody ST2146, thus proving useful in pre-targeting methods involving the combined use of the two antibodies.

SUMMARY OF THE INVENTION

An anti-human tenascin monoclonal antibody has now been found which solves the above-mentioned problems, since it does not possess a non-functional light chain and presents the advantage of additivity when used in combination with another anti-tenascin antibody. This antibody is the object of the present invention, together with the method for obtaining it and its use in therapy, in particular for the preparation of a product useful for the treatment of diseases characterised by the expression of tenascin, such as, for instance, tumours.

The present invention relates to the antibody and to antibody fragments, optionally containing additional markers and diagnostic agents, to processes for obtaining said antibody and antibody fragments, to pharmaceutical compositions containing said antibody and its fragments and to diagnostic and therapeutic methods making use of them, as well as kits useful for implementing said methods.

The present invention also relates to the DNA encoding said antibody or fragments thereof, to vectors containing such DNA, to host cells containing such vectors, to the protein coded for by the nucleotide sequences SEQ ID NO: 1 and SEQ ID NO: 2, to the DNA encoding the protein and the fragments, to the specific complementary determining regions (CDRs) and proteins containing such CDRs. In particular, the object of the present invention is also the hybridoma that produces said monoclonal antibody.

The antibody which is the object of the present invention is characterized by the sequences of the variable region of the light and heavy chains SEQ ID NO:2 and SEQ ID NO:4, respectively, shown in FIGS. 17 and 18. For the sake of brevity, the antibody which is the object of the present invention will be identified by the name ST2485. Also fragments of ST2485 or its chimeric or recombinant derivatives can be produced and used within the scope of the present invention. Also objects of the present invention are the proteolytic fragments of said antibody capable of binding to an antigenic epitope within the A1-4-D region of the human tenascin. In the course of the description of the present invention what is meant by antibody fragments are those fragments capable of binding to an antigenic epitope within the A1-4-D region of the human tenascin C.

According to the present invention, said antibody or proteolytic fragments are preferably biotinylated.

Another object of the present invention consists in the hybridoma cell line, called cST2485, producing the antibody ST2485.

The hybridoma cell line was deposited at the Centro di Biotecnologie Avanzate, Largo Rossana Benzi 10, Genoa, Italy, on 12 Nov. 2003 in accordance with the provisions of the Budapest Treaty, under deposit number PD03003.

Also objects of the present invention are the recombinant derivatives of antibody ST2485, which may optionally be biotinylated. In particular, the recombinant derivatives preferred are those in which the murine constant region is replaced by its human counterpart (Ferrer, C., et al., *J. Biotechnol.*, 52: 51-60, 1996), or those in which the murine constant region is replaced by a biologically active component, such as, for example, a member of the avidin family (Penichet M L., Manuel, L., et al., *J. Immunol.*, 163: 4421-4426, 1999), a growth factor useful for stimulating tumour-directed immunological effectors (for example, G-CSF, GM-CSF), or those in which the murine constant region is replaced by a pharmacologically active component, such as, for example, a superantigen, a toxin, a cytokine or any other protein useful for enhancing the anticancer therapeutic efficacy (Di Massimo, A M, et al., *British J. Cancer*, 75(6):822-828, 1997; Parente D., et al., *Anticancer Research*, 17(6A): 4073-4074, 1997). The methods for obtaining such derivatives are well known to experts in the field.

Another object of the present invention consists in conjugated derivatives of antibody ST2485, optionally biotinylated.

In particular, the conjugated derivatives preferred are those in which the biologically active component is bound to the antibody by means of conventional systems. Examples of biologically active compounds are the members of the avidin family, a growth factor useful stimulating tumour-directed immunological effectors (for example, G-CSF, GM-CSF), or those in which the murine constant region is replaced by a pharmacologically active component, such as, for example, a superantigen, a toxin, a cytokine or any other protein useful for enhancing the anticancer therapeutic efficacy, anticancer drugs, and radioisotopes.

A further object of the present invention consists in the use of the antibody or its derivatives for the preparation of a pharmaceutical product useful in a method for cancer radioimmunotherapy carried out preferably according to the method called three-step pre-targeting, also known by the trade-mark PAGRIT®, including the administration to a subject suffering from a cancer expressing the tenascin antibody ST2485 or proteolytic fragments thereof, preferably biotinylated.

Recombinant derivatives of the antibody which is the object of the present invention and its conjugates can be used to advantage in cancer therapy. Therefore, the use of the antibody and its fragments or derivatives in the preparation of a medicine for the treatment of tumours expressing tenascin constitutes a further object of the present invention.

For the purposes of implementing radioimmunotherapy two therapeutic kits, one systemic and the other locoregional, are also described. These kits are also known by the trade-mark PAGRIT®. The systemic kit consists of 5 vials, including vial 1 containing the bio-tinylated antibody or fragments or derivatives thereof according to the present invention; vial 2 containing avidin; vial 3 containing streptavidin; vial 4 containing biotinylated human albumin; and vial 5 containing biotin DOTA (or derivatives of biotin described in WO 02/066075). The locoregional kits consists of 3 vials, corresponding to vials 1, 2 and 5 of the systemic kit. The vials are prepared so as to be suitable for injection in the subject to be treated, preferably a human subject. For the purposes of implementing radioimmunotherapy, a method called IART (Intraoperative Avidination for Radionuclide Treatment) is described, based on the intraoperative treatment of patients undergoing surgical removal of tumour masses with the reagents which are the object of the present invention, either alone or in combination with other components of the PAGRIT® kit.

The specific container, preferably in the form of a vial suitable for injection containing the antibody or its fragments in biotinylated form, constitutes a further object of the present invention.

According to one embodiment of the present invention, in the therapeutic kits the biotinylated antibody is combined with other anti-tenascin antibodies, preferably directed at the EGF-like region of the protein. Alternatively the biotinylated antibody can be coupled to other antibodies specific to the tumour. A general description of this type of method is to be found in EP 0 496 074, *European Journal of Nuclear Medicine* Vol. 26, No4; April, 1999;348-357, U.S. Pat. No. 5,968,405.

Another object of the present invention is the use of the monoclonal antibody ST2485 for obtaining images for subsequent diagnostic purposes ("imaging") by means of in-vivo immunolocalisation in the tumour.

Another object of the present invention is the use of the monoclonal antibody ST2485 in combination with a second anti-tenascin antibody in a test for the production of a diagnostic kit for determining circulating levels of tenascin.

These and other objects of the present invention will be described in detail here below, also with the aid of examples and figures.

BRIEF DESCRIPTION OF THE FIGURES

FIG. 17: SEQ ID NO: 2 sequence of the variable region of the light chain of ST2485 (VL). Encoded by the nucleic acid shown in SEQ ID NO:1.

FIG. 18: SEQ ID NO: 4 sequence of the variable region of the heavy chain of ST2485 (VH). Encoded by the nucleic acid amino acid shown in SEQ ID NO: 3.

DETAILED DESCRIPTION OF THE INVENTION

Figure 1:
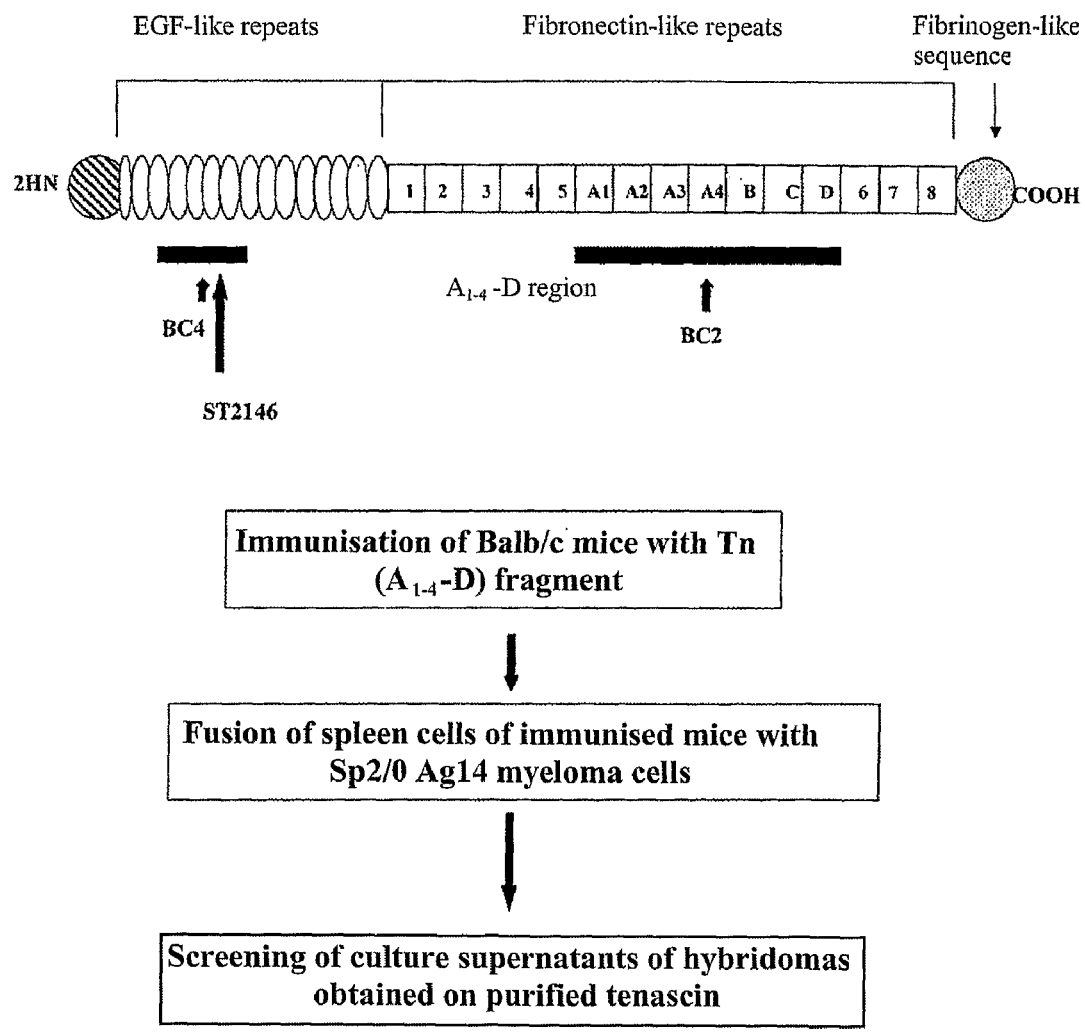
FIG. 1: schematic representation of human tenascin C and the strategy adopted to generate the BC-2-like antibody.

The inventors have prepared a new anti-human tenascin antibody called ST2485, whose light and heavy chain variable region sequences are SEQ ID NO: 2 and SEQ ID NO: 4, respectively, produced from the hybridoma cell line cST2485. The antibody is capable of binding to an antigenic epitope within the $A_{(1-4)}$-D region of human tenascin.

The proteolytic fragments of the antibody according to the present invention are capable of binding to an antigenic epitope within the $A_{(1-4)}$-D region of human tenascin.

Recombinant derivatives of the antibody according to the present invention are obtained according to conventional methods which are well known to experts in the field. The recombinant derivatives preferred are those in which the murine constant region is replaced by its human counterpart, or by a biologically or pharmacologically active component, or by a member of the avidin family.

According to the present invention, the conjugated derivatives are obtained by means of conventional methods well known in this field. The preferred conjugated derivatives are those in which a biologically active portion is bound to the antibody. Examples of biologically active portions are the members of the avidin family, a growth factor useful for stimulating tumour-directed immunological effectors (such as G-CSF, GM-CSF), a pharmacologically active portion, such as, for example, a toxin, superantigen, cytokine or any other protein useful for enhancing the therapeutic anticancer effect, anticancer drugs, and radioisotopes.

For further information regarding the preparation of the recombinant and conjugated derivatives, the reader is referred to WO 03/072608.

According to the present invention, recombinant or conjugated derivatives of the monoclonal antibody are also referred to as "derivatives".

In one preferred embodiment of the present invention, the antibody, its fragments and derivatives can be biotinylated.

The antibody according to the present invention, its fragments and derivatives can also advantageously contain additional markers and diagnostic agents.

The present invention also includes the DNA encoding the monoclonal antibody or its fragments as defined above. The invention also comprises a vector containing said DNA, and a host cell containing said vector.

Vectors and host cells fall within the sphere of the common knowledge pertaining this field.

The present invention also comprises the protein coded for by the nucleotide sequences SEQ ID NO: 1 and SEQ ID NO: 3 or the fragments thereof, and the DNA encoding it.

The present invention also comprises specific CDRs (Complementary Determining Regions) of the above-mentioned antibody and proteins containing said CDRs.

The process for preparing the antibody according to the present invention consists of the following stages:
 a) immunisation of an animal, preferably a mouse, with the $A_{(1-4)}$-D fragment of human tenascin;
 b) fusion of the somatic spleen cells of said animal with myeloma cells not producing immunoglobulins;
 c) selection of the monoclonal antibody.

The monoclonal antibody ST2485 is produced from the hybridoma cell line cST2485, identified above.

According to the present invention, the antibody or its fragments or its derivatives, optionally biotinylated, are used for the preparation of a pharmaceutical product useful for the treatment and diagnosis of diseases characterised by expression of tenascin. In particular, said diseases are tumours, and more particularly include glioma, breast cancer, lung cancer, fibrosarcoma and squamous cell carcinoma.

In one preferred aspect, the above-mentioned pharmaceutical product is used in the two-stage perioperative therapy of solid tumours, described in the International application WO 03/07268. In this type of therapy, the biotinylated antibody is administered, followed by avidin, thus constructing the "artificial receptor" for the actual subsequent anticancer agent. In this case, the anticancer agent will be delivered by biotin, which will be contained in a chemical compound suitable for forming a complex with the anticancer agent and hereinafter referred to as the biotin compound, and will be administered systemically in the postoperative phase. The biotin, in fact, will localise only where avidin is present and in this case we can be sure that avidin is present in the area we are interested in treating, in that it is introduced by the surgeon a few hours earlier (e.g. 4 to 72 hours) during the operation. This is an advantage in that it drastically reduces the time elapsing between removal of the primary tumour and adjuvant therapy.

As regards the industrial aspects of the present invention, the antibody described herein will be suitably formulated in pharmaceutical compositions or therapeutic or diagnostic kits, according to normal practice in the pharmaceutical field.

Pharmaceutical compositions and kits are entirely of the type which is conventional in this field and can be prepared by experts in the field even only on the basis of common knowledge. Examples of pharmaceutical compositions are provided in the references cited in the present invention. The same is true of the kits. Particularly preferred are the kits for tumour radioimmunotherapy, as described in the above-mentioned studies by Paganelli et al., and in EP 0 496 074, WO 02/066075, WO 03/072608, and WO 03/075960. A particular use of the radioimmunotherapy kit can be implemented with the device described in WO 03/069632.

Pharmaceutical compositions containing the antibody or its derivatives or fragments, optionally biotinylated in mixtures with at least one pharmaceutically acceptable excipient or vehicle are included in the scope of the present invention.

In a particular embodiment of the present invention, kits are supplied for systemic radioimmunotherapy, particularly three-step pre-targeting radioimmunotherapy, containing 5 vials, vial 1 containing an antibody or its fragments or recombinant derivatives or its conjugates or analogues, optionally biotinylated; vial 2 containing avidin; vial 3 containing streptavidin; vial 4 containing biotinylated human albumin; and vial 5 containing biotin DOTA.

In another embodiment of the present invention, the kits are for locoregional radioimmunotherapy and contain 3 vials which are the same as vials 1, 2 and 5 of the systemic kit.

In a particularly preferred embodiment, in the vial containing biotin

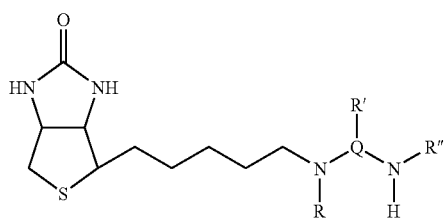

(I)

DOTA, said biotin DOTA is the formula (I) compound in which Q is a —$(CH_2)_n$— group, where n is a whole number from 4 to 12, in which case R' is not present, or Q is selected from the group consisting of —$(CH_2)_a$—$CH(R')_b$—$(CH_2)_b$—, where a and b are independently whole numbers from 0 to n, R' is as defined here below, or Q is cyclohexyl, phenyl, in which case R' is a substituent on the cyclohexyl or phenyl ring;

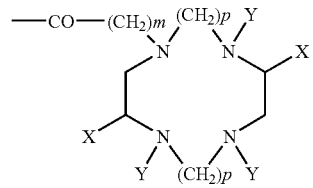

(II)

R is hydrogen or -Λ where -Λ is a formula (II) macrocycle, where the various Y's, which may be the same or different, are selected from the group consisting of hydrogen, straight or branched $C_1$-$C_4$ alkyl, —$(CH_2)_m$—COOH, where m is a whole number from 1 to 3, X is hydrogen, or the group —$CH_2$—U, where U is selected from the group consisting of methyl, ethyl, and p-aminophenyl, or X is the group —$(CHW)_o$—Z, where o is a whole number from 1 to 5, W is hydrogen, methyl or ethyl, Z is a 5-, or 6-member heterocyclic group containing one or more heteroatoms selected from O, N—$R_1$, where $R_1$ is hydrogen or straight or branched $C_1$-$C_4$ alkyl, and S; or Z is selected from the group consisting of —$NH_2$, —NH—C(=NH)—$NH_2$, or —S—$R_2$, where $R_2$ is straight or branched $C_1$-$C_4$ alkyl;
p is the number 2 or 3;
R' is selected from the group consisting of hydrogen, straight or branched $C_1$-$C_4$ alkyl, —$(CH_2)_q$-T, in which T is selected from the group consisting of —S—CHs, —OH, —COOH, and q is the number 1 or 2;
R" has the same meanings as R', upon the following conditions: if R is —Λ, R" is hydrogen; if R is hydrogen, R" is -Λ, or R and R" are, respectively, —$(CH_2)_r$-Λ(for R), where r is a whole number from 4 to 12, and -Λ (for R'), Q being a —$(CH_2)_n$— group, where n is a whole number from 4 to 12.

These compounds are described in WO 02/066075.

In a particularly preferred embodiment, in the vial containing avidin, the latter is an avidin dimer in which two molecules of avidin are bound via —$NH_2$ groups by means of suberate, or an avidin dimer in which two molecules of avidin are bound via —COOH groups by means of polyethylene glycol with a molecular weight of 3,400, as described in WO 03/075960.

In the kits according to the invention, the antibody, its proteolytic fragments, its derivatives, optionally biotinylated, can be in combination with other anti-tenascin antibodies, preferably targeting the EGF-like region of the protein, or in combination with other tumour-specific antibodies.

All the aspects of this invention, in addition to applying to the therapy of tumours expressing tenascin, also apply to the diagnosis of tumours and particularly tumour immunolocalisation procedures, e.g. imaging. Another object of the present invention is a container, preferably in the form of a vial suitable for injection, containing an antibody or its proteolytic fragments or its derivatives, optionally biotinylated, and/or radiolabelled.

In another aspect of the invention, the antibody or its fragments, recombinant derivatives, or analogues are used in combination with a second tenascin-specific antibody, in a sandwich-type in-vitro ELISA assay, in conditions in which said second antibody binds to a second antigenic epitope of tenascin, for the purposes of determining circulating tenascin levels, and particularly the isoforms containing the $A_{(1-4)}$-D region.

The following example further illustrates the invention.

EXAMPLE 1

For the purposes of generating a new hybridoma with BC-2 specificity but not producing a non-functional light chain, Balb/c mice were immunised with the $A_{(1-4)}$-D fragment of human tenascin, containing the epitope recognised by BC-2 (Siri, A., et al., *Nucl. Acid Res.*, 19 (3): 525-531, 1991; Balza, E., et al., *FEBS*, 332: 39-43, 1993). The schematic representation of human tenascin C and the strategy adopted to generate the BC-2-like antibody are illustrated in FIG. 1. Spleen cells of mice immunised with the Tn ($A_{(1-4)}$-D) fragment were fused with myeloma cells not producing immunoglobulins Sp2/0-Ag14 according to standard methods (Cianfriglia, M., et al., *Methods Enzymol.*, 121: 193-210, 1986), and the hybridoma population obtained was subjected to screening by means of the ELISA test on purified tenascin from SK-MeI 28 human melanoma cells (ICLC HTL99010). The hybridomas secreting anti-tenascin antibodies were cloned twice by means of limiting dilutions in growth medium containing FCS and twice in protein-free medium of animal origin (Animal Derived Component Free Medium HyClone, HyQR Perbio).

Production of the ST2485 reference material was achieved by culturing the cST2485 hybridoma cells in a 2-liter bioreactor; two successive limiting dilution subclonings of the cST2485 Post Production Cell Bank (PPCB) led to the selection of the subclone cST2485/A3e/Al2f, used for the production of the Master Cell Bank (MCB) and the Working Cell Bank (WCB).

ST2485 is a mouse immunoglobulin of IgGl/k isotype.

Figure 2:
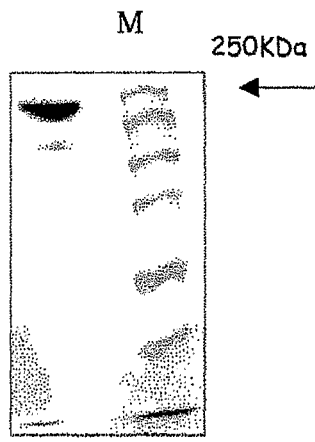
FIG. 2: SDS-PAGE (a,b) and Western blot (c,d) analysis of antibody ST2485 in reducing and non-reducing conditions. In reducing conditions, a double band is observed at the level of the light chain of the antibody (b,d).
Figure 2:
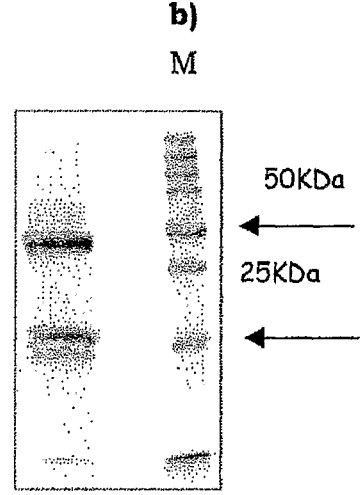
Figure 2:
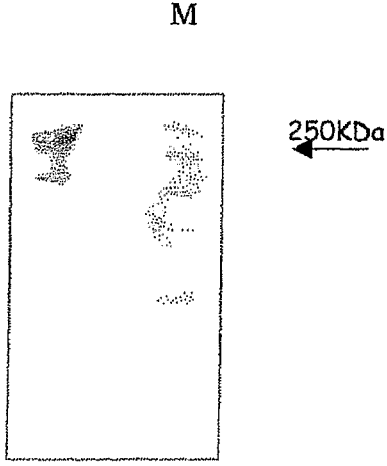
Figure 2:
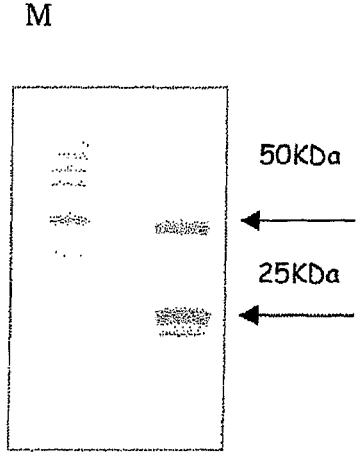
Figure 3:
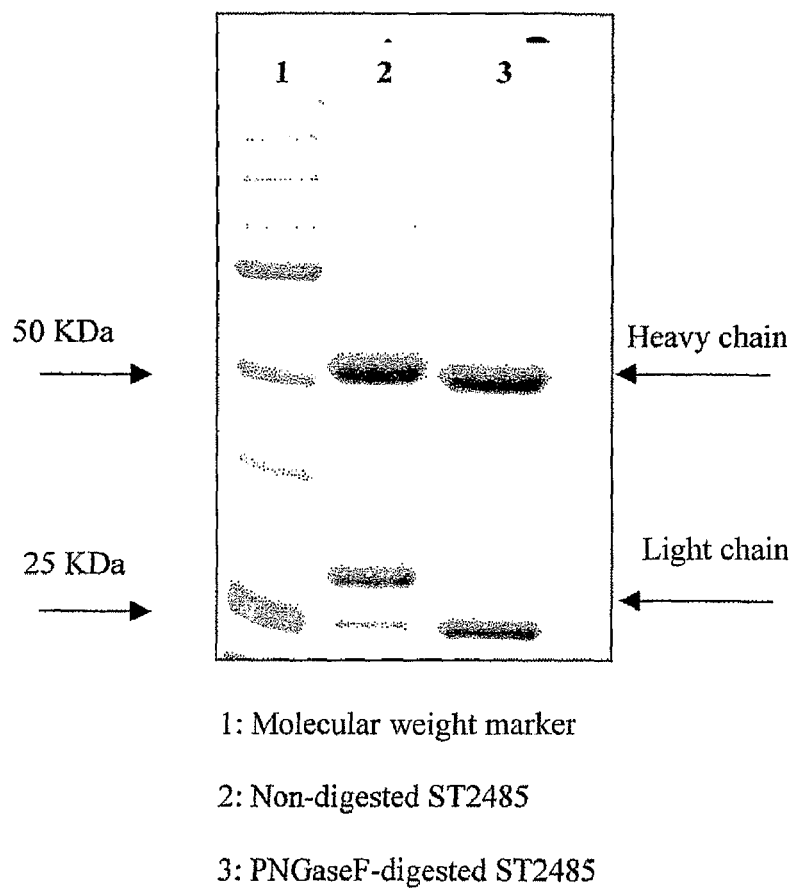
FIG. 3: SDS-PAGE analysis of antibody ST 2485 subjected to deglycosylation by digestion with the enzyme PNGaseF (Peptide-N-Glycosidase from *Flavobacterium*): disappearance of the high molecular weight light chain band is observed.

FIG. 2 shows the SDS-PAGE (a,b) and Western blot (c,d) analysis of the antibody ST2485 in reducing and non-reducing conditions. In reducing conditions (b,d), a double band is observed at the level of the light chain of the antibody; Western blot analysis demonstrates that the two bands are immunoreactive as light chains of immunoglobulin. Hydroxyapatite chromatographic analysis of antibody ST2485, shown in FIG. 3, confirms a mild heterogeneity of the antibody through the slightly asymmetrical peak. In the same analysis, on the other hand, the antibody BC-2 presents a distinctly heterogeneous profile, in which three peaks can be distinguished, of which only peak 1 corresponds to the totally functional homogeneous antibody.

To define the nature of the heterogeneity of antibody ST 2485, a sample of the latter was subjected to digestion of the N-glycoside residues with the enzyme PNGaseF (Peptide-N-glycosidase from *Flavobacterium*). The enzyme digestion was done using the Prozyme deglycosylation kit (cat. No. GE51001), in the conditions indicated by the manufacturer: approximately 8 µg of ST2485 and 5 mU of enzyme were reacted overnight at 37° C. in 10 µl of reaction mixture. Antibody ST2485, digested and undigested, was run on 12% polyacrylamide gel in reducing conditions. The gel was stained with Coomassie Brilliant Blue.

Figure 4:
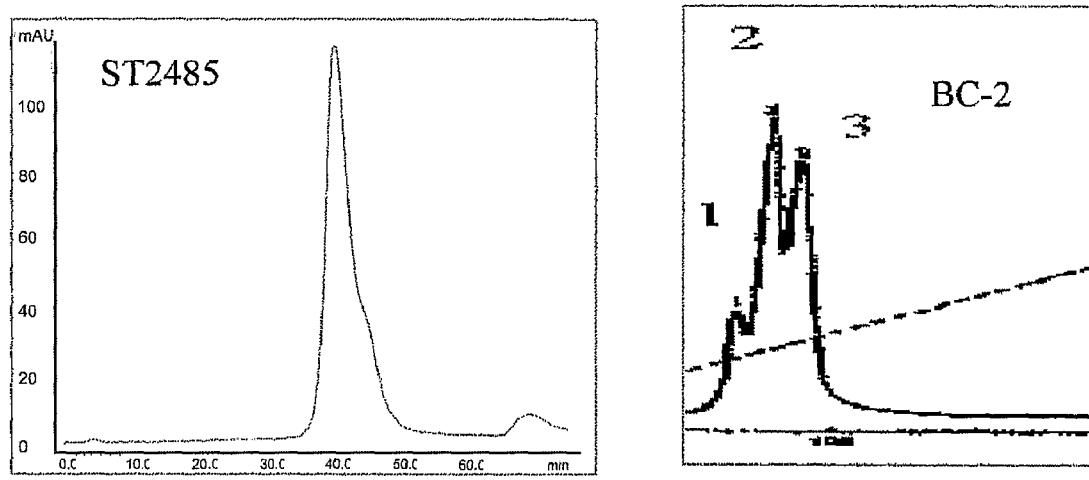
FIG. 4: hydroxyapatite chromatography profiles of antibodies ST2485 and BC-2.

The digestion caused the disappearance of the high molecular weight light chain band, as demonstrated by the SDS-PAGE analysis in reducing conditions illustrated in FIG. 4. This finding shows that the two light chain bands of antibody ST2485 correspond to the glycosylated (high molecular weight) and non-glycosylated (low molecular weight) variants of the same. The existence of a potential N-glycosylation site was also confirmed by the immunoglobulin cDNA sequence data (FIG. 17).

The variable region of the kappa light chain was amplified by the circularised cDNA using a pair of primers (5' GGGAA-GATGGATACA-GTTGGTG (SEQ ID NO: 5), 5' CAA-GAGCTTCAACAGGAATGAG) (SEQ ID NO: 6) that recognise the constant region of the antibody as described by M Sassano et al. *Nucl. Ac. Res.* (1994) 22, 1768-1769.

Figure 5:
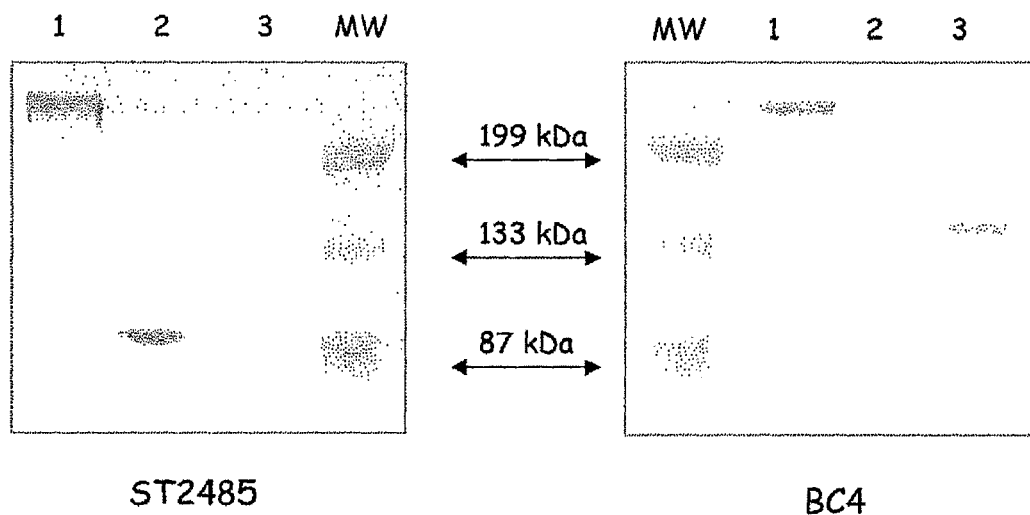
FIG. 5: binding specificity of ST2485 for human tenascin and for the Tn ($A_{(1-4)}$-D) fragment by means of Western blot analysis.

ST2485 binding to the $A_{(1-4)}$-D region of tenascin is specific, as demonstrated by the Western blot analysis presented in FIG. 5. The antibody binds to human tenascin and to the $A_{(1-4)}$-D fragment, but not to the EGF-like fragment of the same protein, containing the epitope recognised by the BC-4 antibody.

Figure 6:
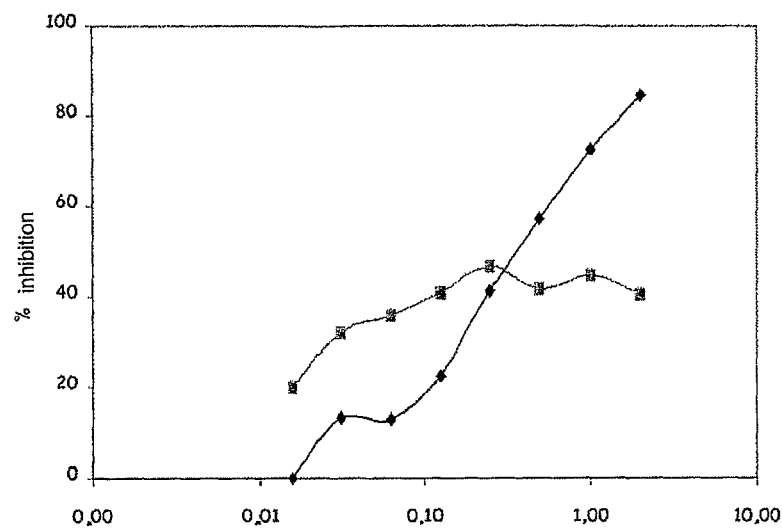
FIG. 6: Competitive ELISA between ST2485 and BC-2 for binding to tenascin C (a) or to the Tn ($A_{(1-4)}$-D) fragment (b).
Figure 6:
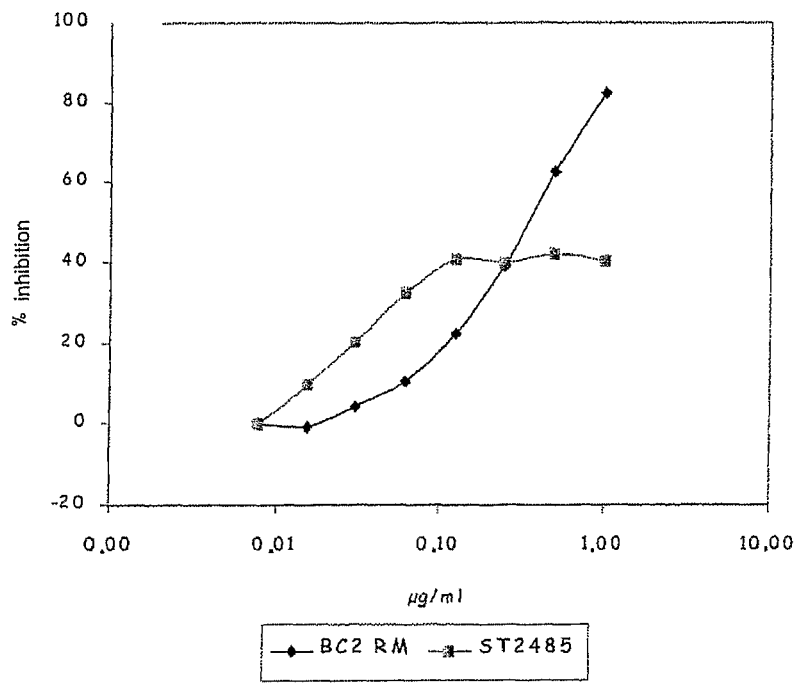

Antibody ST2485 binds human tenascin in a distinct epitope or in one partly shared with BC-2, as demonstrated by the competitive ELISA assay between the two antibodies illustrated in FIG. 6. The biotinylated antibody BC-2, at a concentration established in preliminary experiments, is dispensed with non-biotinylated BC-2 (curve 1) or ST2485 (curve 2) in increasing concentrations on plates sensitised with the antigen tenascin C (a), or Tn $A_{(1-4)}$-D fragment (b). The binding of the biotinylated antibody is measured after addition of HRP-streptavidin and the related chromogenic substrate TMB. Antibody ST2485 causes 40% inhibition of BC-2 binding to tenascin C or the Tn $A_{(1-4)}$-D fragment.

Figure 7:
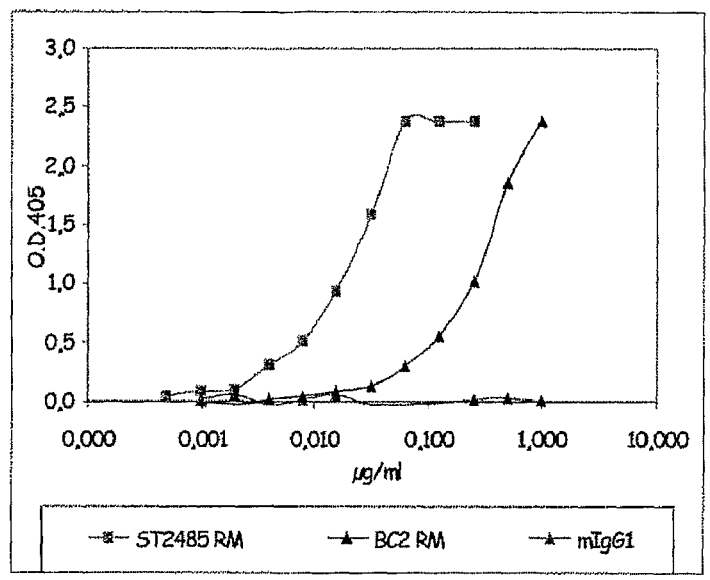
FIG. 7: immunoreactivity of ST2485 compared to BC-2 on tenascin C (a) and on the Tn ($A_{(1-4)}$-D) fragment (b).
Figure 7:
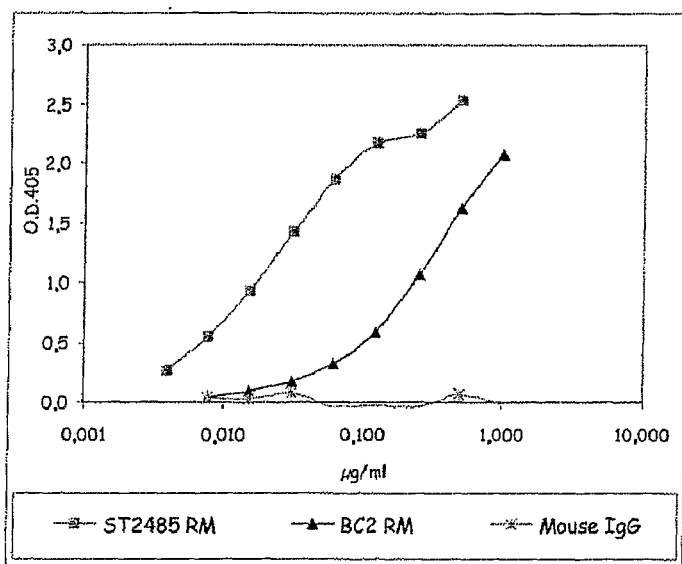

The immunoreactivity of ST2485 was evaluated in comparison with BC-2 by ELISA assay on tenascin C and on the Tn $A_{(1-4)}$-D fragment, as shown in FIG. 7. The antibodies ST2485 and BC-2 and the normal mouse immunoglobulins (nMIgG) were dispensed at increasing concentrations on plates sensitised with tenascin C (a) or with the Tn $A_{(1-4)}$-D fragment (b); the addition of the secondary antimouse antibody labelled with alkaline phosphatase and the related chromogenic substrate (pNPP) made it possible to determine the dose-response curve of the antibodies. The amount of ST2485 necessary to obtain 1.0 OD is approximately 13 times less than the amount of BC-2 on whole tenascin (a), and approximately 10 times less than the amount of BC-2 on the Tn (A1-4-D) fragment (b).

The affinity of antibody ST2485 was evaluated both on tenascin C and on the Tn ($A_{1-4}$-D) fragment by means of BIAcore analysis. On tenascin C the $KD_1$ of ST2485 is $9.77 \times 10^{-10}$ M ($ka_1 = 6.02 \times 10^5$; $kd_1 = 5.88 \times 10^{-4}$), whereas the $KD_1$ of BC-2 is $2.54 \times 10^{-7}$ M ($ka_1 = 9.85 \times 10^3$; $kd_1 = 2.5 \times 10^{-3}$). On the Tn ($A_{1-4}$-D) fragment the $KD_1$ of ST2485 is $9.72 \times 10^{-10}$ M ($ka^1 = 3.28 \times 10^5$; $kd1 = 3.19 \times 10^{-4}$) whereas the $KD_1$ of BC-2 is $7.39 \times 10^{-8}$ M ($ka1 = 2.68 \times 10^{-4}$; $kd_1 = 1.93 \times 10^{-3}$).

Figure 8:
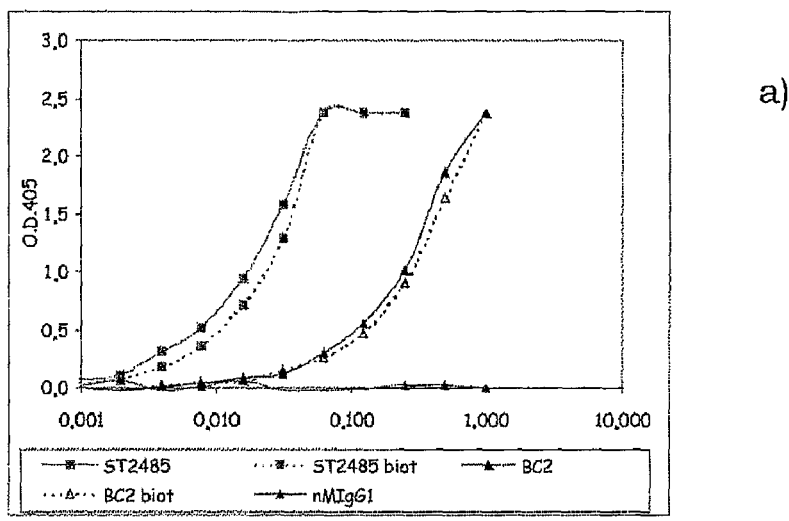
FIG. 8: immunoreactivity of biotinylated ST2485 and BC-2 on tenascin C (a) and on the Tn ($A_{(1-4)}$-D) fragment (b).
Figure 8:
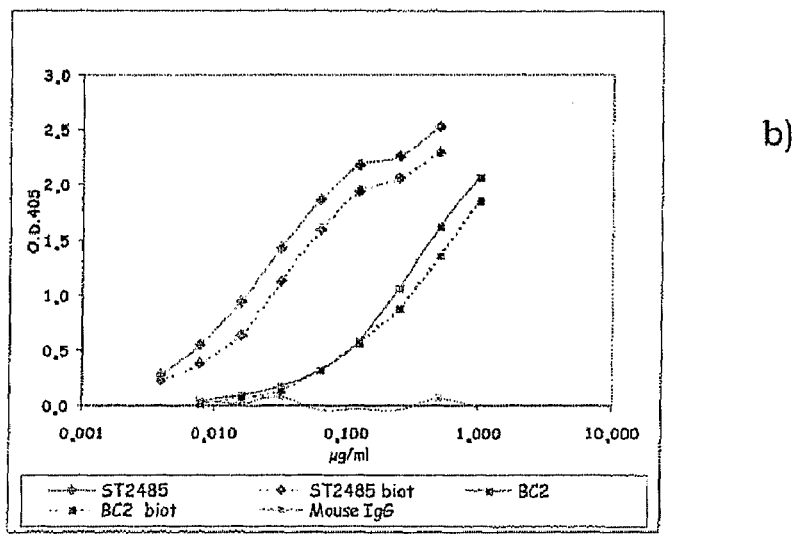

Maintaining the immunoreactivity after biotinylation constitutes a fundamental requisite of the antibody used in pretargeting, and therefore the behaviour of biotinylated ST2485 (8.3 biotins/molecule) was evaluated by ELISA and BIAcore assays in comparison with biotinylated BC-2 (7.6 biotins/molecule). With reference to FIG. 8, the antibodies ST2485 and BC-2, biotinylated and non-biotinylated, and the normal mouse immunoglobulins (nMIgG) were dispensed at increasing concentrations on plates sensitised with tenascin C (a) or with the Tn $A_{(1-4)}$-D fragment (b); the addition of the secondary anti-mouse antibody labelled with alkaline phosphatase and the related chromogenic substrate (pNPP) made it possible to determine the dose-response curve of each biotinylated antibody compared to the non-biotinylated one (residual immunoreactivity). The residual immunoreactivity of biotinylated ST2485 and BC-2 on tenascin C is equal to 76% and 88%, respectively. On the Tn $A_{(1-4)}$-D fragment, the residual immunoreactivity for ST2485 and BC-2 is 73% and 83%, respectively.

The BIAcore analysis of the biotinylated antibodies on whole tenascin shows a $KD_1$ affinity=$2.88 \times 10^{-9}$ M for biotinylated ST2485 ($ka_1 = 2.8 \times 10^5$; $kd_1 = 8.07 \times 10^{-4}$) and a $KD_1$ affinity=$3.71 \times 10^{-7}$ M for biotinylated BC-2 ($ka_1 = 6.0 \times 10^3$; $kd_1 = 2.23 \times 10^{-3}$). Biotinylated ST2485 thus maintains good immunoreactivity and affinity characteristics, conserving an affinity for tenascin approximately 100 times greater than that of biotinylated BC-2.

Figure 9:
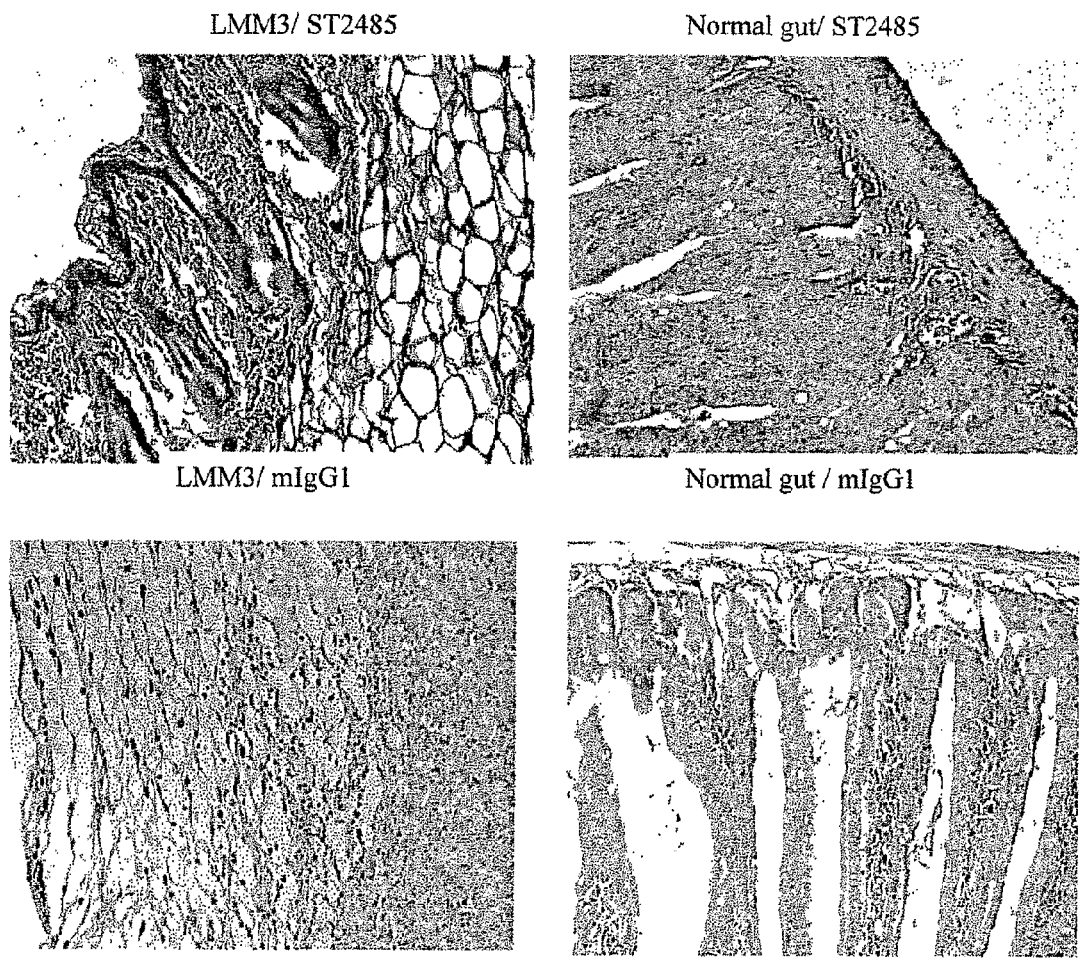
FIG. 9: cross-reactivity of antibody ST2485 with the murine tenascin expressed in LMM3 tumour (murine breast cancer) and in normal murine intestine.

Immunohistochemical studies on various human tumours (breast, lung, stomach, colon) have demonstrated localisation of ST2485 at the level of the extracellular matrix, similar to that reported for BC-2 (Natali, P G, et al., *Int. J. Cancer,* 47 : 811-16, 1991). These studies have also demonstrated the ability of ST2485 to produce cross-reaction with murine tenascin, including that expressed in normal mouse tissues, as can be seen in FIG. 9. Sections of LMM3 tumour (murine mammary carcinoma) and normal murine intestine fixed in formalin were incubated with 10 µg/ml of ST2485 or of normal murine IgG1 antibody (control). After incubation with the biotinylated secondary anti-mouse antibody and the avidin-biotin-peroxidase complex (Vectastain Elite ABC kit) binding to tenascin was detected with the addition of the colorimetric substrate DAB (Vector). The contrast was done with Mayer's haematoxylin. The LMM3 and murine intestine sections are positive with ST2485 but not with the control antibody. It was not possible to perform these studies in comparison with BC-2 since that antibody does not recognise fixed tissue sections embedded in paraffin. The ability of ST2485 to recognise murine tenascin, including that expressed by normal tissues, enhances the significance of the results obtained in the antibody biodistribution studies in the murine model described here below.

Figure 10:
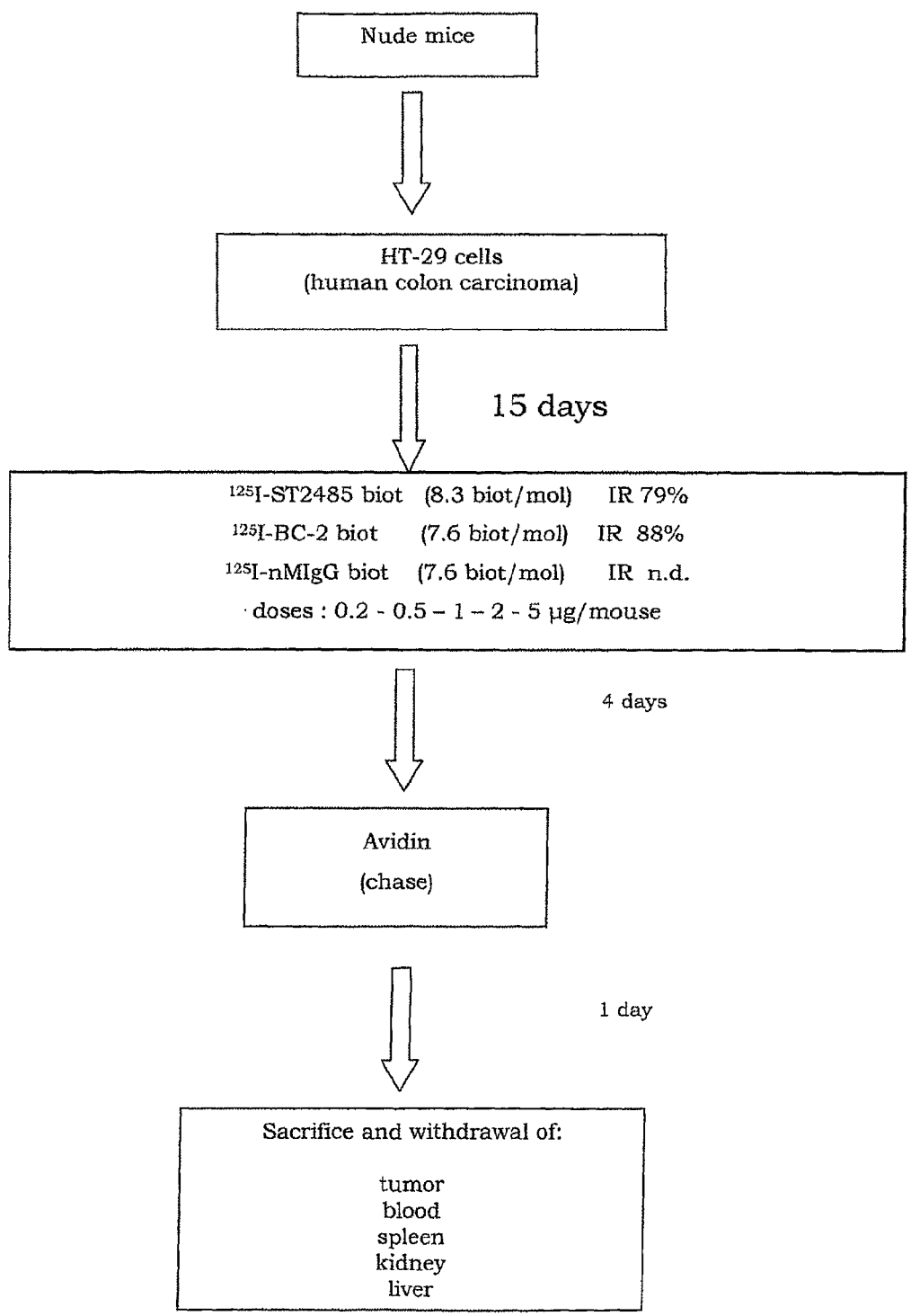
FIG. 10: protocol adopted for the ST2485 biodistribution study in nude mice.

For the purposes of evaluating the ability of the antibody to localise in the tumour mass, biodistribution studies of biotinylated $^{125}$I-labelled ST2485 and BC-2 were carried out. These studies were conducted in nude mice which had been implanted with human tumours expressing tenascin, according to the protocol represented schematically in FIG. 10.

The animals were subcutaneously inoculated with $4 \times 10^6$ human colon carcinoma HT-29 cells in 0.1 ml of sterile saline solution. After 15 days, when the tumour had reached a mass of approximately 200 mg, groups of five animals received intravenous administrations of $^{125}$I-BC2, $^{125}$I-ST2485, or normal mouse $^{126}$I-immunoglobulins (nMIg), all biotinylated (7-9 biotins/mol) and at five different doses: 0.2-0.5-1-2-5 µg/mouse in 100 µl of sterile PBS. Five days after administration of the antibodies the animals were sacrificed and samples of blood, spleen, kidney, liver and tumour were taken for determining the radioactivity present. Twenty-four hours prior to the sacrifice the animals received an intravenous administration of avidin in 100 µl of sterile PBS, at doses 100 times greater than that of the antibody (chase).

Figure 11:
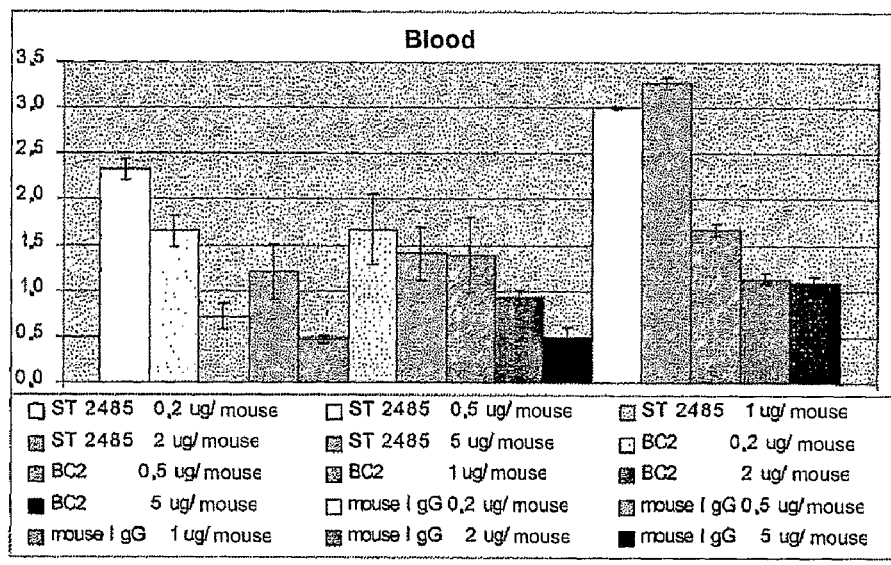
FIGS. 11 and 11a: biodistribution of ST2485 at various administration doses compared with BC-2. The accumulation of ST2485 in the tumour, at all doses administered, is at least twice as much as that of BC-2.
Figure 11:
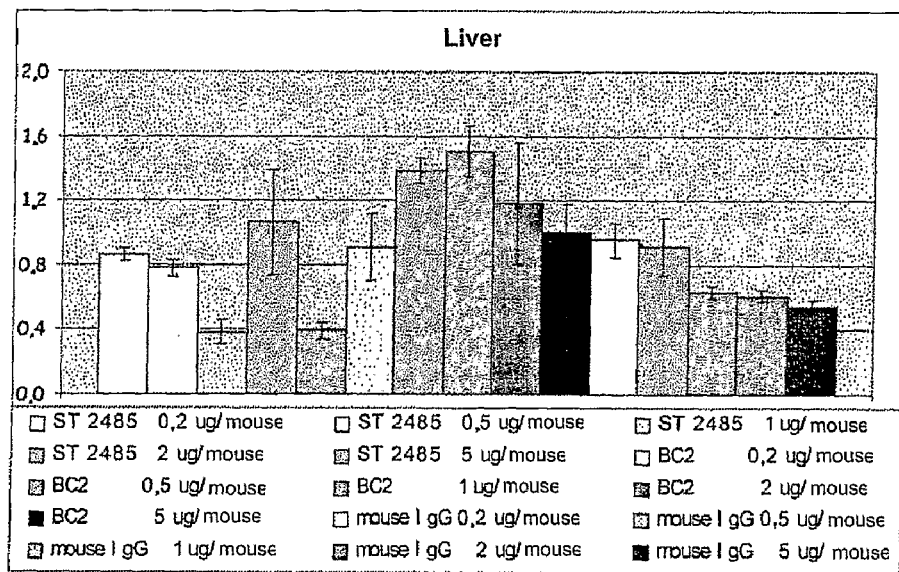
Figure 11A:
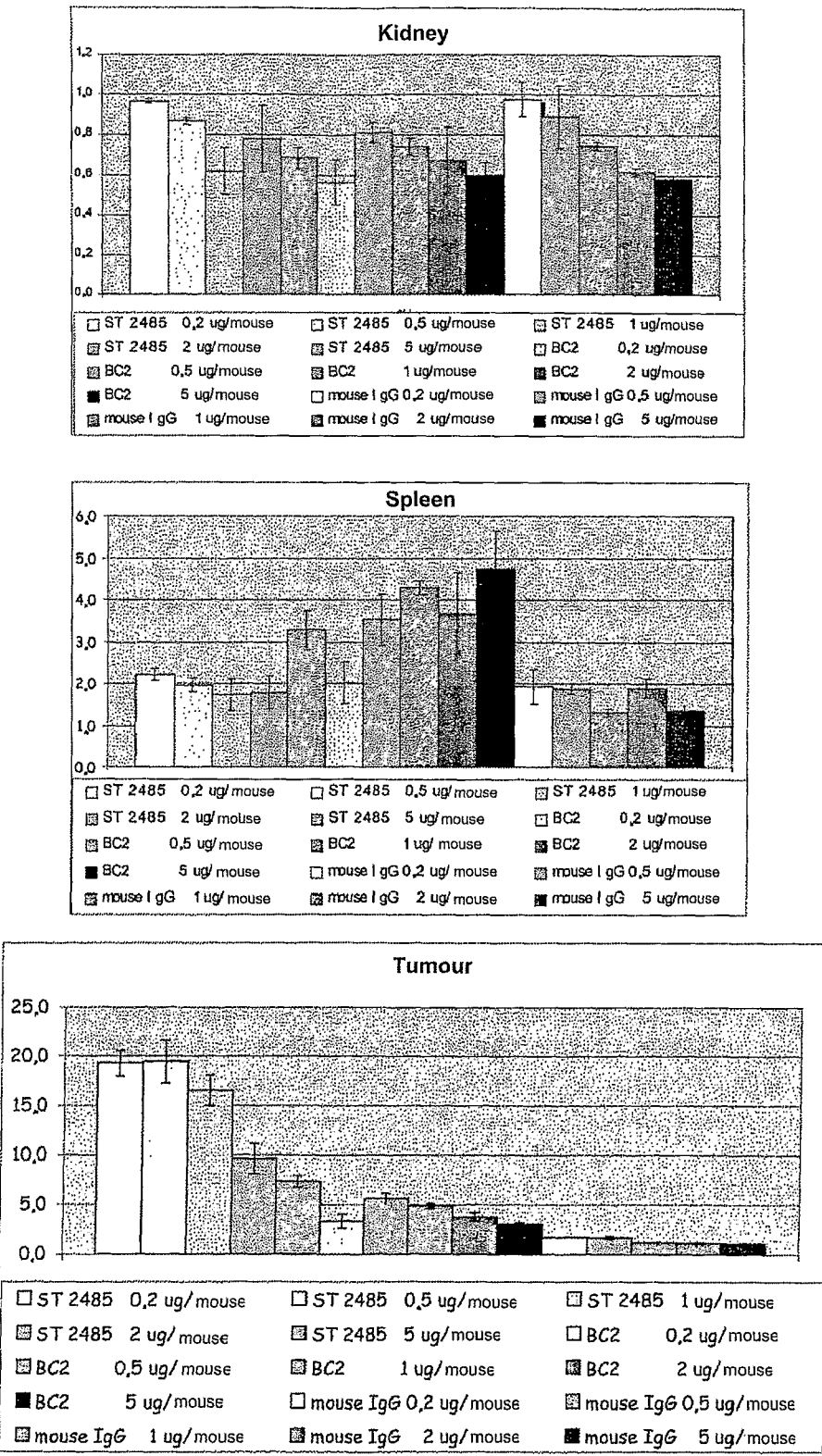
Figure 12:
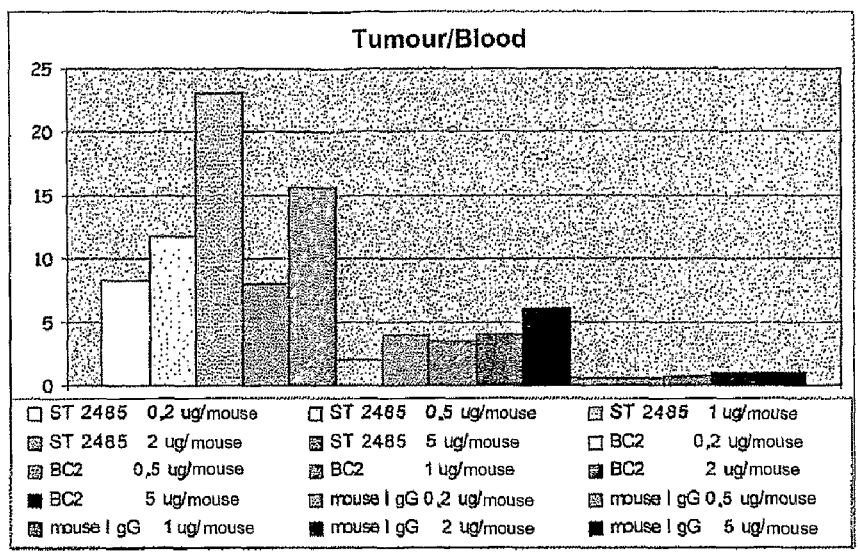
FIGS. 12 and 12a: tumour to non-tumour ratios of ST2485 compared with BC-2. These ratios are higher for antibody ST2485, at all doses administered.
Figure 12:
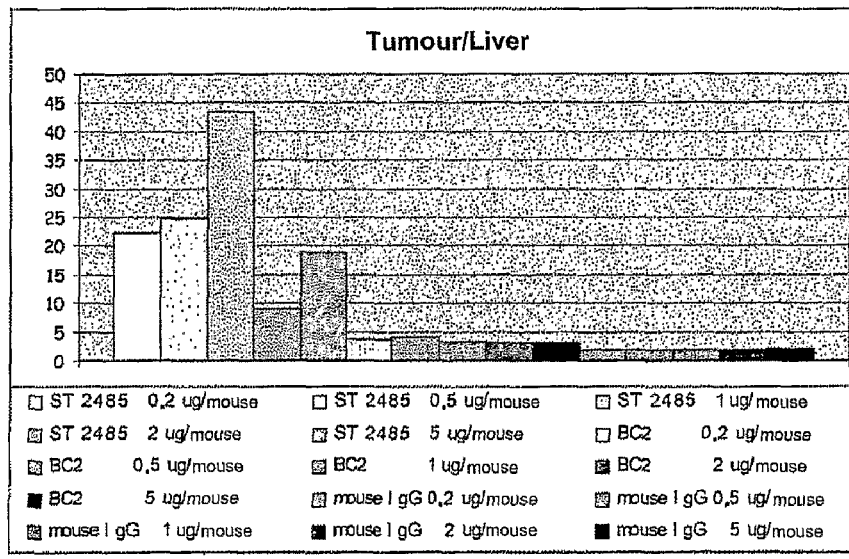
Figure 12A:
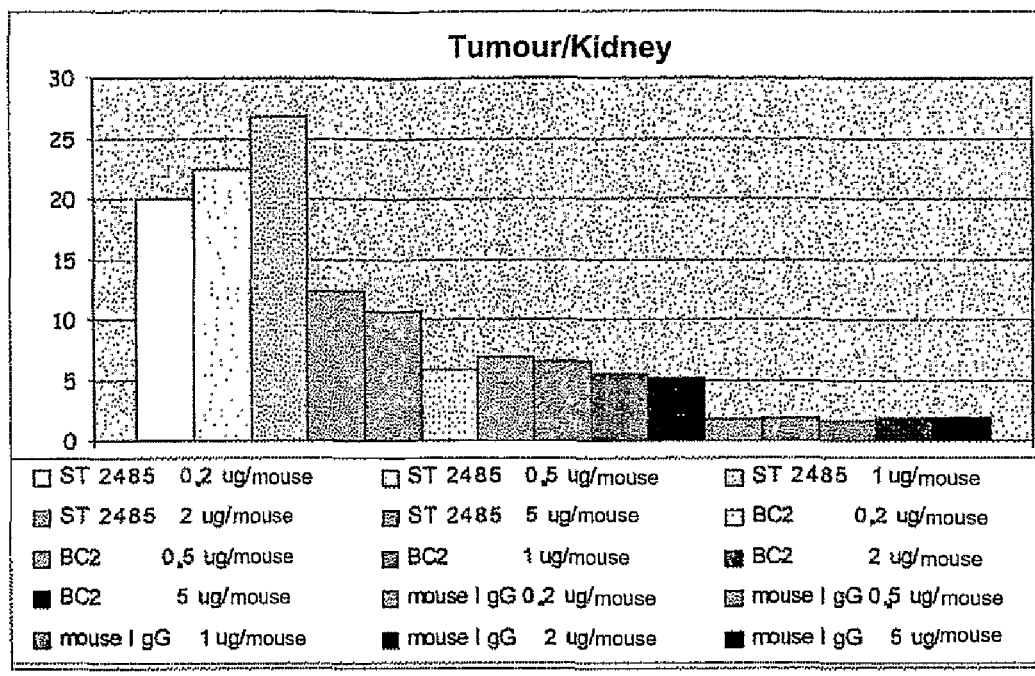
Figure 12A:
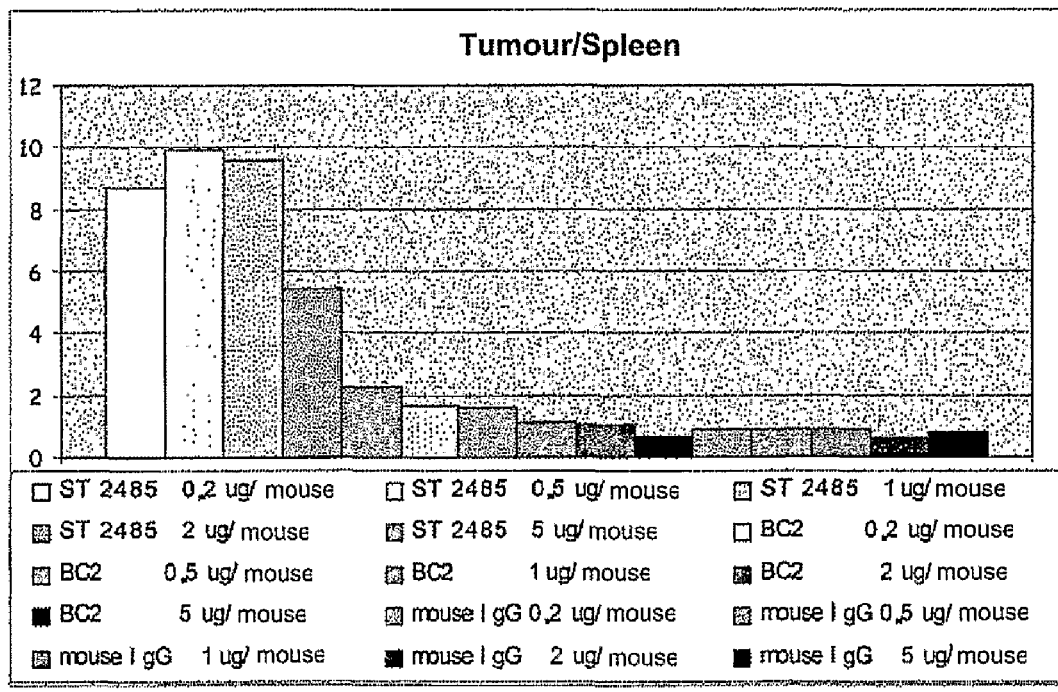

The results, presented in FIGS. 11 and 11a, show that both BC-2 and ST2485 localise specifically in the tumour, regardless of the dose (the amounts of antibody are expressed as percentage of the dose injected per gram of tissue: % ID/gr). Moreover, ST2485 shows a greater localisation in the tumour compared with BC-2 at all doses assayed, always maintaining a higher tumour to non-tumour ratio (FIGS. 12 and 12a). In particular, at the dose of 1 µg/mouse the accumulation of ST2485 in the tumour is equal to 16% of the injected dose, whereas the accumulation of BC-2 does not exceed 5% at any of the doses assayed. At the dose of 1 µg/mouse the tumour: blood ratio for ST2485 is greater than 20 (optimal dose), whereas for the antibody BC-2 this ratio never exceeds 6 at any of the doses assayed. In the other organs, the tumour to non-tumour ratios for ST2485 at the dose of 1 µg/mouse are 9, 26, and 43 in relation to the spleen, kidney and liver, respectively. For BC-2, on the other hand, these ratios are always lower than 7, at all the doses assayed. The tumour to non-tumour ratios are shown in FIGS. 12 and 12a.

Figure 13:
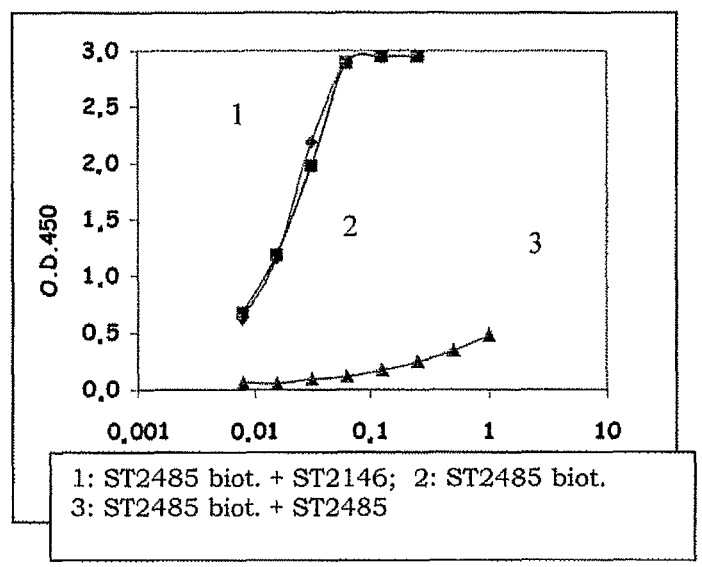
FIG. 13: in-vitro interference (a) and additivity testing (b) of anti-tenascin antibodies ST2485 and ST2146 by means of ELISA test.
Figure 13:
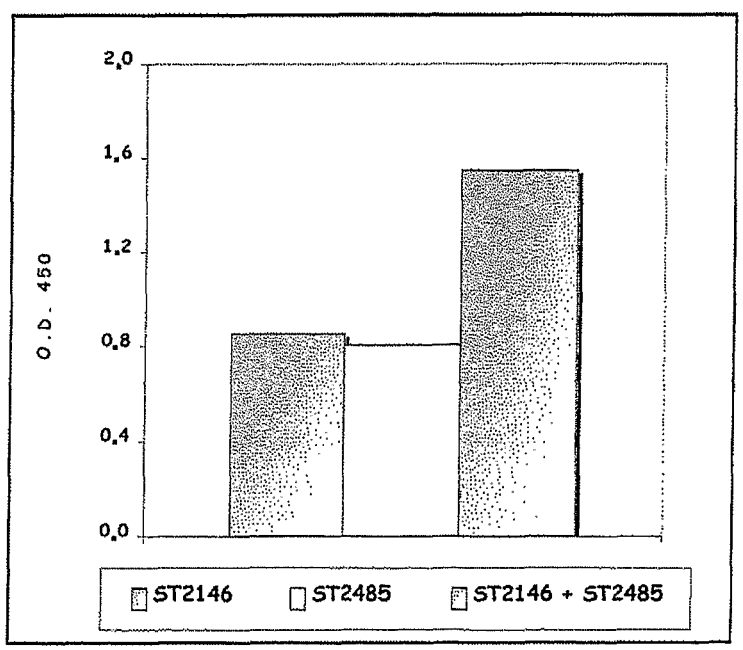

For the purposes of evaluating the possibility of the combined use of the anti-tenascin antibodies ST2485 and ST2146 in the PAGRIT® and TART methods, ST2416 being directed at an epitope localised in the EGF-like region of the protein (De Santis, R., et al., *Br. J. Cancer,* 88: 996-1003, 2003, WO 03/072608), in-vitro and in-vivo additivity experiments were conducted with the two antibodies. FIG. 13, in two ELISA tests performed, on plates sensitised with tenascin C, shows the absence of epitope interference between the antibodies ST2485 and ST2146 (13a) and the additive nature of their binding to the antigen (13b). For the evaluation of the interference (a) biotinylated antibody ST2485, at increasing concentrations, was dispensed on microplates sensitised with tenascin C in the absence (1) and in the presence (2) of ST2146 at saturating concentration: the superimposed curves 1 and 2 indicate the absence of epitope interference between the two antibodies, in that the binding of biotinylated ST2485 to tenascin is not affected by the presence of ST2146 (and vice versa; data not shown). Curve 3 shows the signal obtained when seeding biotinylated ST2485 in the presence of non-biotinylated saturating ST2485 (control).

FIG. 13b shows the additivity test, in which the biotinylated antibodies ST2485 and ST2146 were dispensed, in saturating doses, separately or together, on microplates sensitised with tenascin C: the mixture of the two antibodies produces a signal equal to the sum of the signals, thus demonstrating that the binding of the two antibodies is additive.

Figure 14:
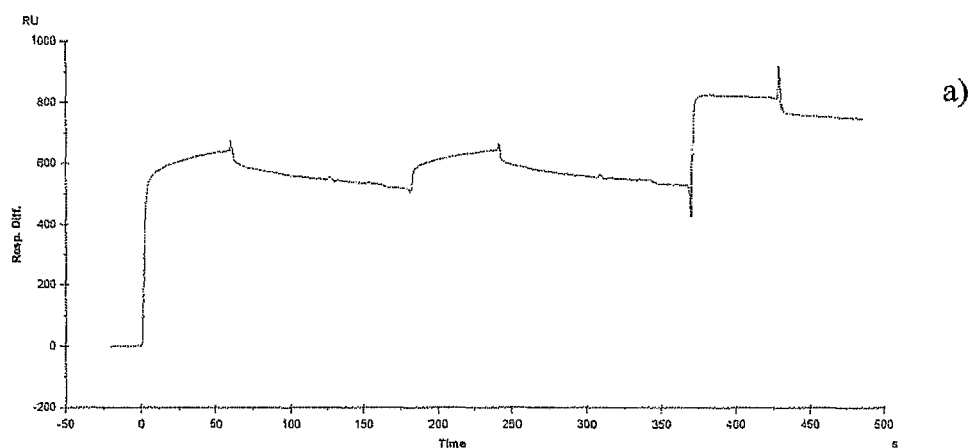
FIGS. 14 and 14a: in-vitro additivity test of antibodies ST2485 and ST2146 by means of BiaCore analysis.
Figure 14:
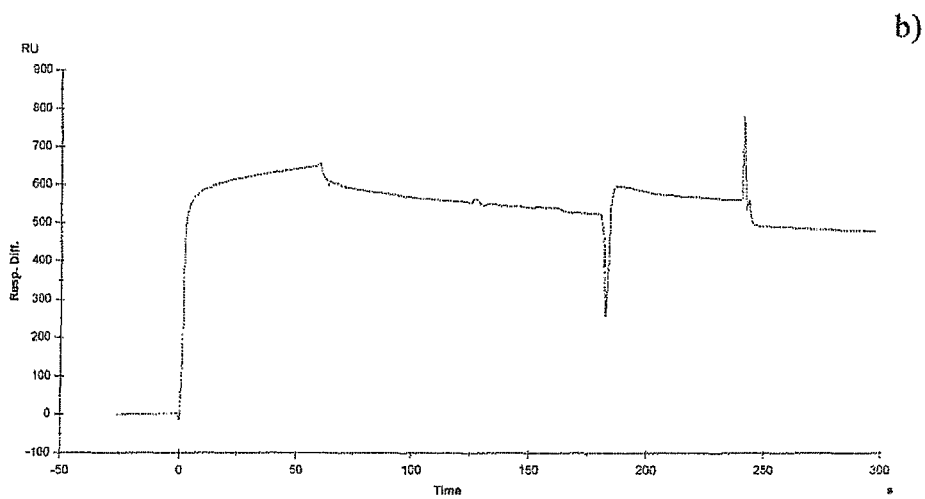
Figure 14A:
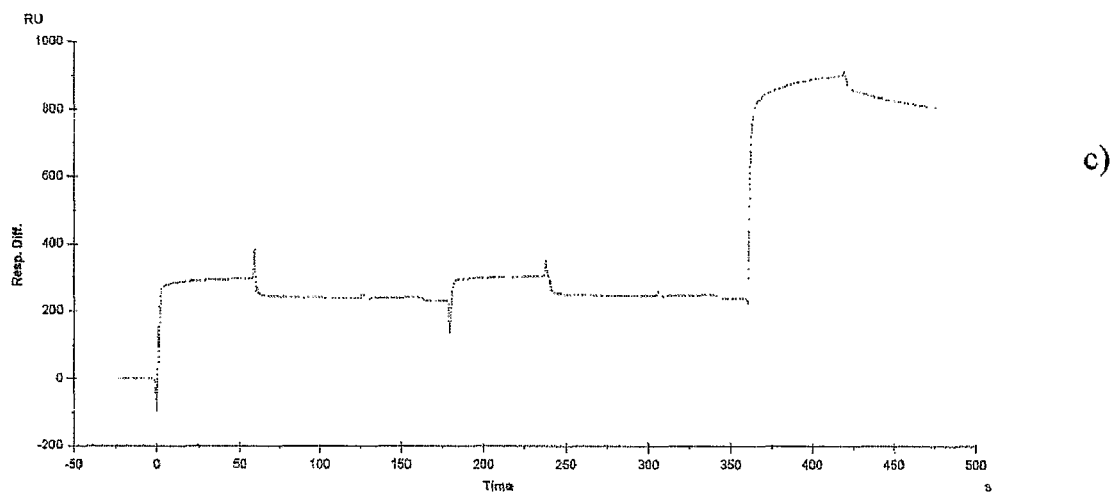
Figure 14A:
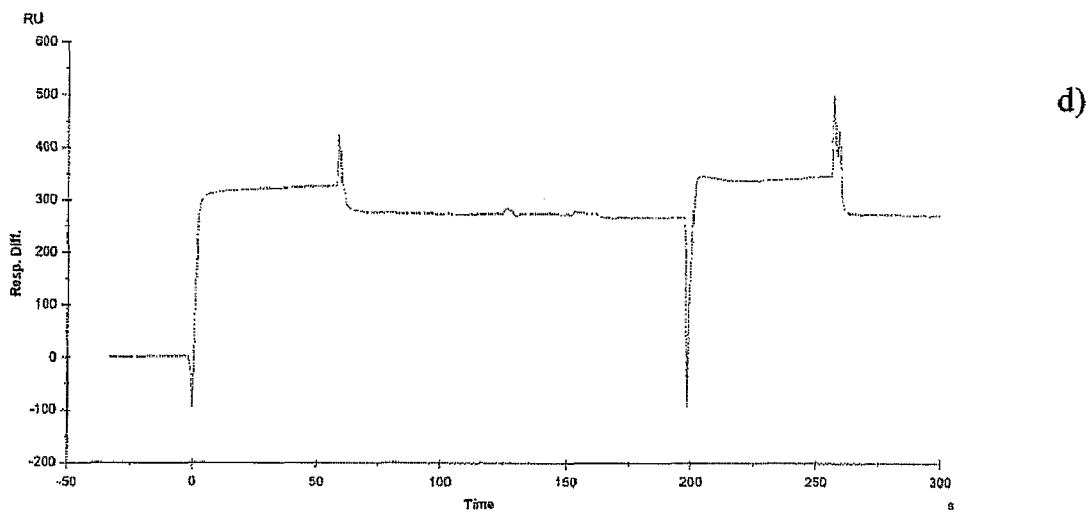

The in-vitro additivity of the two antibodies was also assayed using BIACore analysis, as shown in FIGS. 14 and 14a. The tenascin was immobilised on the chip (CM5 sensor chip, Biosense) according to the method described (De Santis R.; et al.; *Br. J. Cancer,* 88: 996-1003, 2003). Two consecutive injections of the first antibody were administered (ST2485 in a, ST2146 in c) at saturating concentrations (10 □M), followed by injection of the second anti-tenascin antibody (ST2146 in a; ST2485 in c). Sensorgrams a) and c) show that the two antibodies are capable of binding to the respective epitopes in an additive manner, as shown by the increase in the resonance signal produced by each single antibody. Sensorgrams b) and d) represent the injections of ST2485 and ST2146 respectively, each followed by the respective isotypical control antibodies, mIgG2b and mIgG1.

Figure 15:
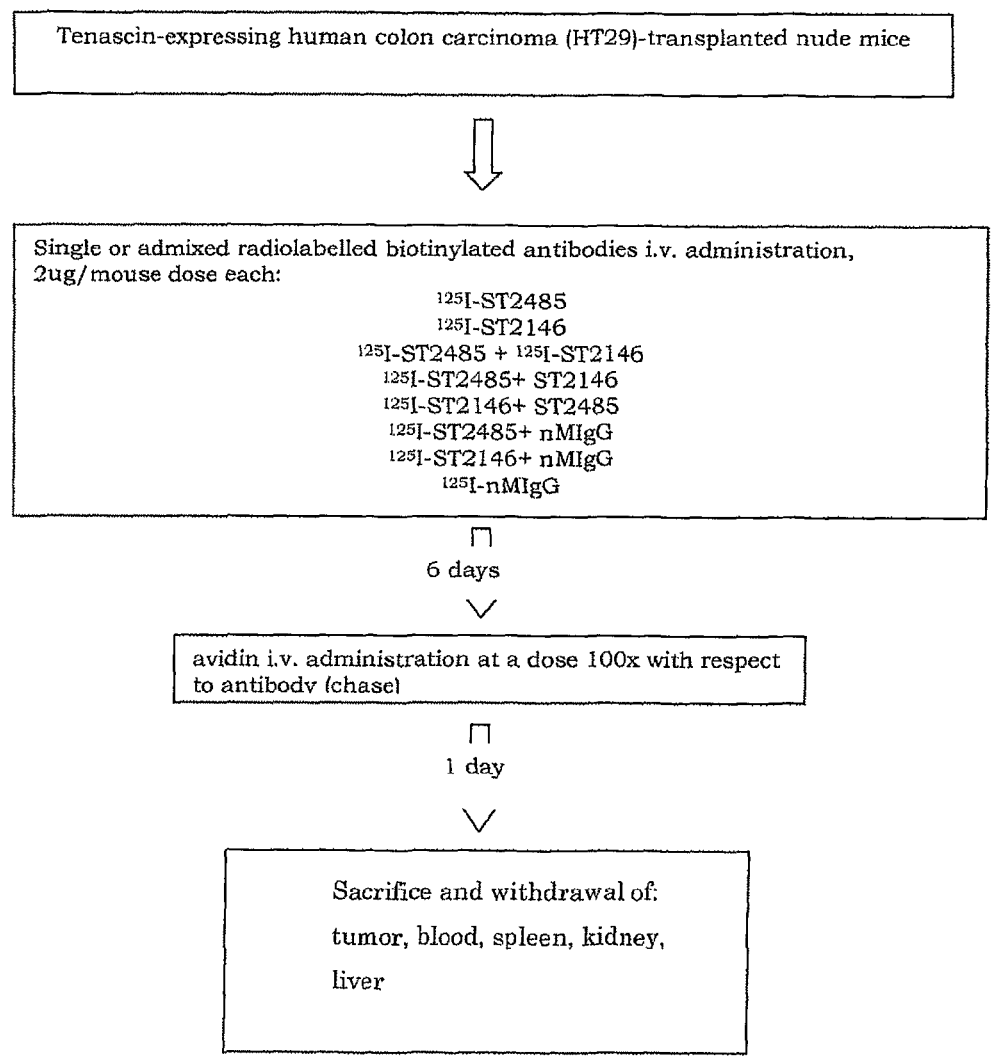
FIG. 15: scheme adopted in the in-vivo additivity study of antibodies ST2485 and ST2146.
Figure 16:
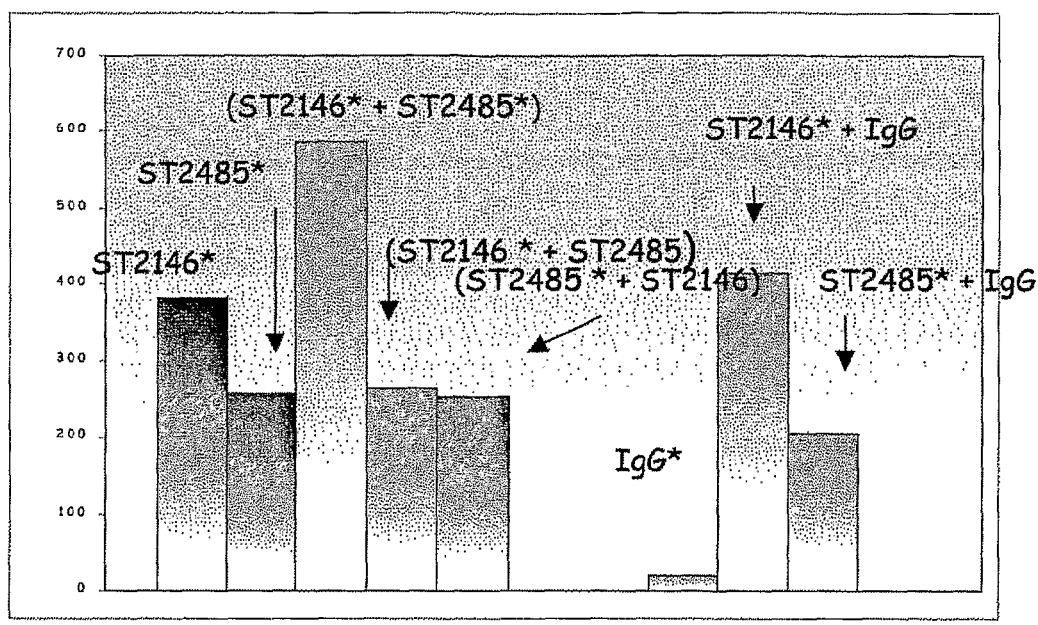
FIG. 16: in-vivo additivity of antibodies ST2485 and ST2146, expressed in ng of antibody localised per gram of tumour.

The additivity study of the two antibodies ST2485 and ST2146 was also conducted in-vivo in the previously described animal model. The study scheme is illustrated in FIG. 15, whereas the results obtained are presented in FIG. 16, expressed in ng of antibody per gram of tumour. The data confirm the additivity of the two antibodies also in the animal model. The mixture of the two labelled antibodies, in fact, presents an accumulation in the tumour amounting to 93% of the theoretical value (mathematical sum of the two individual labelled antibodies). Groups of control animals were treated with mixtures of radiolabelled antibody and second "cold" antibody to avoid any interference.

The variable region of the kappa light chain was amplified starting from the circularised cDNA using a pair of primers (5' GGGAAGATGG-ATACAGTTGGTG 3' (SEQ ID NO: 5), 5' CAAGAGCTTCAACAGGAAT-GAG 3') (SEQ ID NO: 6) that recognise the constant region of the light chain of the antibody, as described by M. Sassano, et al., *Nucl. Ac. Res.,* (1994) 22, 1768-1769.

The variable region of the gamma heavy chain was amplified starting from the circularised cDNA using a pair of primers (5' ATGGAGTTAG-TTTGGGCAGCAG 3' (SEQ ID NO: 7), 5' GCACAACCACCATACTGAG-AAG 3') (SEQ ID NO: 8) that recognise the constant region of the heavy chain of the antibody, as described by M. Sassano, et al., *Nucl. Ac. Res.,* (1994) 22, 1768-1769.

FIG. 17 shows the SEQ ID NO: 2 sequence of the variable region of the light chain (VL) of ST2485.

FIG. 18 shows the SEQ ID NO: 4 sequence of the variable region of the heavy chain (VH) of ST2485.

The comparative characterisation of ST2485 compared to BC-2 demonstrates that the antibody ST2485 possesses the following characteristics:

it recognises an epitope within the $A_{(1-4)}$-D region of human tenascin, close to or partly overlapping that of BC-2;

it is a homogeneous antibody as regards the composition of the light and heavy chain, in that the heterogeneity observed is due to light chain glycosylation variants;

it is more immunoreactive than BC-2;

it has greater affinity for the antigen than BC-2;

it is comparable to BC-2 as regards the maintenance of immunoreactivity after biotinylation;

it is superior to BC-2 as regards tumour localisation in the animal model;

it binds in an additive manner with the anti-tenascin monoclonal antibody ST2146 to tenascin C, both in-vitro and in-vivo in the animal model.

REFERENCES

Balza E., Siri A., Ponassi M., Caocci F., Linnala A., Virtanen I., Zardi L. Production and characterization of monoclonal antibodies specific for different epitopes of human tenascin. FEBS, 332: 39-43, 1993.

Bourdon M. A., Wikstrand C. J., Furthmayr H., Matthews T. J., Bigner D. D. Human glioma-mesenchymal extracellular matrix antigen defined by monoclonal antibody. Cancer Res., 43 (6): 2796-2805, 1983.

Chinol M., Casalini P., Maggiolo M., Canevari S., Omodeo E. S., Caliceti P., Veronese F. M., Cremonesi M., Chiolerio F., Nardone E., Siccardi A. G., Paganelli G. Biochemical modifications of avidin improve pharmacokinetics and biodistribution, and reduce immunogenicity. British Journal of Cancer, 78 (2): 189-197, 1998.

Chiquet-Ehrismann R, Mackie E. J., Pearson C. A., Sakakura T. Tenascin: an extracellular matrix protein involved in tissue interactions during fetal development and oncogenesis. Cell, 47 (1): 131-139, 1986.

Cianfriglia M., Mariani M., Armellini D., Massone A., Lafata M., Presentini L. and Antoni G. Methods for high frequency production of soluble antigen-specific hybridomas; specificities and affinities of monoclonal antibodies obtained. Methods Enzymol., 121: 193210, 1986.

Cremonesi M., Ferrari M., Chinol M., Stabin M. G., Grana C., Prisco G., Robertson C., Tosi G., Paganelli G. Three-step radioimmunotherapy with yttrium-90 biotin: dosimetry and pharmacokinetics in cancer patients. Eur. J. Nucl. Med., 26 (2): 110-120, 1999.

De Santis R., Anastasi A. M., D'Alessio V., Pelliccia A., Albertoni C., Rosi A., Leoni B., Lindsdedt R., Petronzelli F., Dani M., Verdoliva A., Ippolito A., Campanile A., Manfredi V., Esposito A., Cassani G., Chinol M., Paganelli G. and Carminati P. Novel antitenascin antibody with increased localisation for Pretargeted Antibody-Guided RadioimmunoTherapy (PAGRIT). Br. J. Cancer, 88, 996-1003, 2003.

Di Massimo A. M., Di Loreto M., Pacilli A., Raucci G., D'Alatri L., Mele A., Bolognesi A., Polito L., Stirpe F. and De Santis R. Immunoconjugates made of an anti-EGF-receptor Monoclonal Antibody and Type 1 RIPs from *Saponaria* ocymoides or *Vaccaria* pyramidata. Br. J. Cancer, 75 (6): 822-828, 1997.

Ferrer C., Anastasi A. M., Di Massimo A. M., Bullo A., Di Loreto M., Raucci G., Pacilli A., Rotondaro L., Mauro S., Mele A. and De Santis R. Expression and characterization of a mouse/human chimeric antibody specific for EGF receptor. J. Biotechnol., 52: 51-60, 1996.

Grana C., Chinol M., Robertson C., Mazzetta C., Bartolomei M., De C$_1$cco C., Fiorenza M., Gatti M., Caliceti P. and Paganelli G. Pretargeted adjiuvant radioimmunotherapy with Yttrium-90-biotin in malignant glioma patients: a pilot study. Br. J. Cancer, 86: 207-212, 2002.

Natali P G., Nicotra M. R., Bigotti A., Botti C., Castellani P., Risso A. M. and Zardi L. Comparative analysis of the expression of the extracellular matrix protein tenascin in normal human fetal, adult and tumor tissues. Int. J. Cancer, 47: 811-816, 1991.

Paganelli G., Bartolomei M., Ferrari M., Cremonesi M., Broggi G., Maira G., Sturiale C., Grana C., Prisco G., Gatti M., Caliceti P., Chinol M. Pre-targeted locoregional radioimmunotherapy with 90Y-biotin in glioma patients: Phase I study and preliminary therapeutic results. Cancer Biother. & Radiopharm., 16 (3): 227-235, 2001.

Paganelli G., Grana C., Chinol M., Cremonesi M., D e Cicco C., D e Braud F., Robertson C., Zurrida S., Casadio C., Zoboli S., Siccardi A. G., Veronesi U. Antibody-guided three step therapy for high grade glioma with yttrium-90 biotin. Eur. J. Nucl. Med., 26 (4): 348-357, 1999.

Paganelli G., Magnani P., Zito F., Lucignani G., Sudati F., Truci G., Motti E., Terreni M., Polo B., Giovanelli M. Pre-targeted immunodetection in glioma patients: tumor localization and single-photon emission tomography imaging of [99 mTc]PnAO-biotin. Eur. J. Nuci. Med., 21 (4): 314-21, 1994.

Parente D., D'Alatri L., Di Massimo A. M., Saccinto M P., Novelli S., Pacilli A., Mele A. and De Santis R. Production and in-vitro characterization of a recombinant immunotoxin made of a single chain anti-EGF receptor antibody and a type ribosome-inactivating protein (RIP) from filamentous fungus *Aspergillus* clavatus. Anticancer Research, 17 (6A): 4073-4074, 1997.

Penichet, M L., Kang Y S., Pardridge W M., Morrison S L., and Shin S. U. An antibody-avidin fusion protein specific for the transferrin receptor serves as a delivery vehicle for effective brain targeting: initial applications in anti-HIV antisense drug delivery to the brain 1. J. Immunol., 163: 4421-4426, 1999.

Ramos D. M., Chen B., Regezi J., Zardi L, Pytela R. Tenascin-C matrix assembly in oral squamous cell carcinoma. Int. J. Cancer, 75: 680-687, 1998.

Riva P., Arista A., Sturiale C., Moscatelli G., Tison V., Mariani M., Seccamani E., Lazzari S., Fagioli L., Franceschi G., et al. Treatment of intracranial human glioblastoma by direct administration of 131I-labelled anti-tenascin monoclonal antibody BC-2. Int. J. Cancer, 51 (1): 7-13, 1992.

Riva P., Franceschi G., Arista A., Frattarelli M., Riva N., Cremonini A. M., Giuliani G., Casi M. Local application of radiolabeled monoclonal antibodies in the treatment of high grade malignant glioma: a six-year clinical experience. Cancer, 80 (12 Suppl): 2733-42, 1997.

Riva P., Franceschi G., Frattarelli M., Riva N., Guiducci G., Cremonini A. M., Giuliani G., Casi M., Gentile R., Jekunen A. A., Kairemo K. J. 131I radioconjugated antibodies for the locoregional radioimmunotherapy of high-grade malignant glioma—phase I and II study. Acta Oncol., 38(3):351-9, 1999.

Siri A., Carnemolla B., Saginati M., Leprini A., Casari G., Baralle F. and Zardi L. Human tenascin: primary structure, pre-mRNA splicing patterns and localization of the epitope recognized by two monoclonal antibodies. Nucl. Acid Res., 19 (3): 525-531, 1991.

The invention claimed is:

1. An isolated anti-human tenascin monoclonal antibody or a proteolytic fragment thereof, comprising a light chain variable region of SEQ ID NO:2 and a heavy chain variable region of SEQ ID NO:4, wherein said light chain variable region and said heavy chain variable region are capable of binding to an antigenic epitope within the $A_{(1-4)}$-D region of human tenascin.

2. The fragment of the antibody according to claim 1, further containing additional markers and diagnostic agents.

3. The antibody or the fragment thereof according to claim 1, wherein said antibody or said fragment thereof are biotinylated.

4. An isolated antibody or a fragment thereof coded for by the nucleotide sequences SEQ ID NO:1 and SEQ ID NO:3.

5. Hybridoma producing the antibody according to claim 1, deposited at the Centro di Biotecnologie Avanzate, Largo Rossana Benzi 10 Genoa - Italy on 12 November 2003 in accordance with the provisions of the Budapest Treaty, with the accession number PD03003.

6. Process for the preparation of the antibody according to claim 1 comprising
a) immunizing an animal with the $A_{(1-4)}$-D fragment of human tenascin;
b) fusing somatic spleen cells of said animal with myeloma cells not producing immunoglobulins;
c) selecting the monoclonal antibody.

7. A pharmaceutical or diagnostic composition containing an antibody or a proteolytic fragment thereof according to claim 1, with at least one pharmaceutically acceptable vehicle or excipient.

8. A kit for systemic radioimmunotherapy consisting of 5 vials: wherein vial 1 contains the antibody or the proteolytic fragment thereof according to claim 1; vial 2 contains avidin; vial 3 contains streptavidin; vial 4 contains biotinylated human albumin; and vial 5 contains biotin DOTA.

9. A kit for locoregional radioimmunotherapy consisting of 3 vials; wherein vial 1 contains the antibody or the proteolytic fragment thereof according to claim 1, vial 2 contains avidin; and vial 3 contains biotin DOTA.

10. The kit according to claim 8 wherein said biotin DOTA in vial 5 is the formula (I) compound

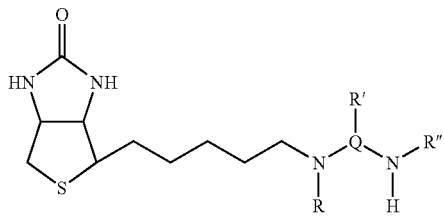

in which Q is a —$(CH_2)n$-group, where n is a whole number from 4 to 12, in which case R' is not present, or Q is selected from the group consisting of —$(CH_2)_a$—CH$(R')_b$—$(CH_2)_b$—, where a and b are independently whole numbers from 0 to n, wherein n is as defined above, R' is as defined here below, or Q is cyclohexyl, phenyl, in which case R' is a substituted on the cyclohexyl or phenyl ring;

R is hydrogen or -Λ where -Λ is a formula (II) macrocycle

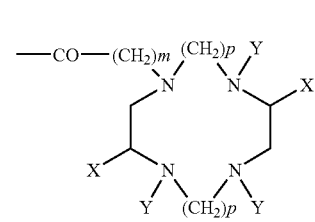

where the various Y's which may be the same or different, are selected from the group consisting of hydrogen, straight or branched $C_1$—$C_4$ alkyl, —$(CH_2)_m$—COOH, where m is a whole number from 1 to 3, X is hydrogen, or the group —$CH_2$—U, where U is selected from the group consisting or methyl, ethyl, and p-aminophenyl, or X is the group —$(CHW)_o$—Z, where o is a whole number from 1 to 5, W is hydrogen, methyl or ethyl, Z is a 5- or 6- member heterocyclic group containing one or more heteroatoms selected from O, N—$R_1$, where $R_1$ is hydrogen or straight or branched $C_1$-$C_4$ alkyl, and S; or Z is selected from the group consisting of —$NH_2$, —NH—C(=NH)—$NH_2$, or —S—$R_2$, where $R_2$ is straight or branched $C_1$-$C_4$ alkyl;

p is the number 2 or 3;

R' is selected from the group consisting of hydrogen, straight or branched $C_1$-$C_4$ alkyl, —$(CH_2)_q$-T, in which T is selected from the group consisting of —S—$CH_3$, —OH, —COOH, and q is the number 1 or 2;

R" has the same meanings as R', upon the following conditions: if R is -Λ, R" is hydrogen, if R is hydrogen, R" is -Λ, or R and R" are, respectively —$(CH_2)_r$-Λ(for R), where r is a whole number from 4to 12, and -Λ(for R'), Q being a —$(CH_2)_n$— group, where n is a whole number from 4 to 12.

11. The kit according to claim 8, in which vial 3 contains an avidin dimer in which two avidin molecules are bound via the —$NH_2$ groups by means of suberate.

12. The kit according to claim 8, in which said vial 3 contains an avidin dimer in which two avidin molecules are bound via the —COOH groups by means of polyethylene glycol with a molecular weight of 3,400.

13. The kit according to claim 8, in which the antibody or the proteolytic fragment thereof are combined with other anti-tenascin antibodies.

14. The kit according to claim 8, wherein the antibody or the proteolytic fragment thereof are combined with other tumor-specific antibodies.

15. Container containing the antibody or the proteolytic fragment thereof according to claim 1.

16. Combination comprising the antibody or the proteolytic fragment thereof according to claim 1, and a second tenascin-specific antibody.

17. An isolated murine anti-human tenascin monoclonal antibody or a proteolytic fragment thereof comprising a light chain variable region of SEQ ID NO:2 and a heavy chain variable region of SEQ ID NO:4, wherein said light chain variable region and said heavy chain variable region are capable of binding to an antigenic epitope within the $A_{(1-4)}$-D region of human tenascin.

18. An antibody or a fragment thereof according to claim 17 comprising a human constant region.

19. The kit according to claim 9 wherein in which said biotin DOTA
in vial 2 is the formula (I) compound

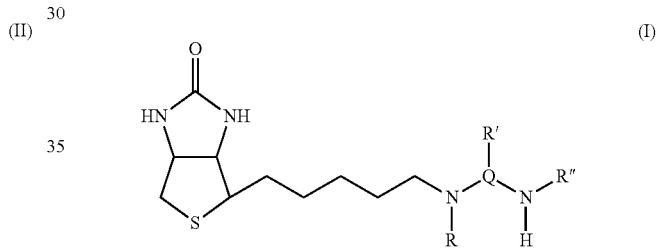

in which Q is a —$(CH_2)n$—group, where n is a whole number from 4 to 12, in which case R' is not present, or Q is selected from the group consisting of —$(CH_2)_a$—CH$(R')_b$—$(CH_2)_b$—, where a and b are independently whole numbers from 0 to n, wherein n is as defined above, R' is as defined here below, or Q is cyclohexyl, phenyl, in which case R' is a substituted on the cyclohexyl or phenyl ring;

R is hydrogen or -Λ where -Λ is a formula (II) macrocycle

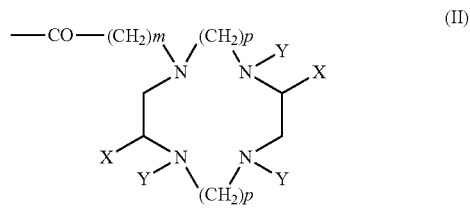

where the various Y's which may be the same or different, are selected from the group consisting of hydrogen, straight or branched $C_1$-$C_4$ alkyl, —$(CH_2)_m$—COOH, where m is a whole number from 1 to 3, X is hydrogen, or the group —$CH_2$—U, where U is selected from the group consisting or methyl, ethyl, and p-aminophenyl, or X is the group —$(CHW)_o$-Z, where o is a whole number from 1 to 5, W is hydrogen, methyl or ethyl, Z is a 5- or 6- member heterocyclic group containing one or more heteroatoms selected from O, N—$R_1$, where $R_1$ is hydrogen or straight or branched $C_1$-$C_4$ alkyl, and S; or Z is selected from the group consisting of —$NH_2$, —NH—C(=NH)—$NH_2$, or —S—$R_2$, where $R_2$ is straight or branched $C_1$-$C_4$ alkyl;

p is the number 2 or 3;

R' is selected from the group consisting of hydrogen, straight or branched $C_1$-$C_4$ alkyl, —$(CH_2)_q$-T, in which T is selected from the group consisting of —S—$CH_3$, —OH, —COOH, and q is the number 1 or 2;

R" has the same meanings as R', upon the following conditions: if R is -Λ, R" is hydrogen, if R is hydrogen, R" is -Λ, or R and R" are, respectively —$(CH_2)_r$-Λ(for R), where r is a whole number from 4 to 12, and -Λ(for R'), Q being a —$(CH_2)_n$— group, where n is a whole number from 4 to 12.

* * * * *

SEQUENCE LISTING

<160> NUMBER OF SEQ ID NOS: 8

<210> SEQ ID NO 1
<211> LENGTH: 393
<212> TYPE: DNA
<213> ORGANISM: Mus musculus
<220> FEATURE:
<221> NAME/KEY: CDS
<222> LOCATION: (1)..(393)

<400> SEQUENCE: 1

```
atg gat ttt caa gtg cag att ttc agc ttc ctg cta atc agt gct tca      48
Met Asp Phe Gln Val Gln Ile Phe Ser Phe Leu Leu Ile Ser Ala Ser
1               5                   10                  15 gtc ata atg tcc aga gga caa att gtt ctc tcc cag tct cca gca atc      96
Val Ile Met Ser Arg Gly Gln Ile Val Leu Ser Gln Ser Pro Ala Ile
                20                  25                  30 ctg tct gca tct cca ggg gag aag gtc aca atg act tgc agg gcc aac     144
Leu Ser Ala Ser Pro Gly Glu Lys Val Thr Met Thr Cys Arg Ala Asn
            35                  40                  45 tca agt gta cgt ttc atg cac tgg tac cag cag aag cca gga tcc tcc     192
Ser Ser Val Arg Phe Met His Trp Tyr Gln Gln Lys Pro Gly Ser Ser
        50                  55                  60 ccc aaa ccc tgg att tat gcc aca tcc aac ctg gct tct gga gtc cct     240
Pro Lys Pro Trp Ile Tyr Ala Thr Ser Asn Leu Ala Ser Gly Val Pro
65                  70                  75                  80 gct cgc ttc agt ggc agt ggg tct ggg acc tct tat tct gtc aca atc     288
Ala Arg Phe Ser Gly Ser Gly Ser Gly Thr Ser Tyr Ser Val Thr Ile
                85                  90                  95 agc aga gtg gag gct gaa gat gct gcc act tat tac tgc cag cag tgg     336
Ser Arg Val Glu Ala Glu Asp Ala Ala Thr Tyr Tyr Cys Gln Gln Trp
                100                 105                 110 agt agt aat tca ccc agg acg ttc ggt gga ggc acc aag gtg gaa atc     384
Ser Ser Asn Ser Pro Arg Thr Phe Gly Gly Gly Thr Lys Val Glu Ile
            115                 120                 125 aga cgg gct                                                         393
Arg Arg Ala
    130
```

<210> SEQ ID NO 2
<211> LENGTH: 131
<212> TYPE: PRT
<213> ORGANISM: Mus musculus

<400> SEQUENCE: 2

```
Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
                20                  25                  30

Leu Ser Ala Ser Pro Gly Glu Lys Val Thr Met Thr Cys Arg Ala Asn
            35                  40                  45

Ser Ser Val Arg Phe Met His Trp Tyr Gln Gln Lys Pro Gly Ser Ser
        50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Tyr Ser Val Thr Ile
                85                  90                  95

Ser Arg Val Glu Ala Glu Asp Ala Ala Thr Tyr Tyr Cys Gln Gln Trp
                100                 105                 110
```

```
Ser Ser Asn Ser Pro Arg Thr Phe Gly Gly Gly Thr Lys Val Glu Ile
        115                 120                 125

Arg Arg Ala
    130

<210> SEQ ID NO 3
<211> LENGTH: 414
<212> TYPE: DNA
<213> ORGANISM: Mus musculus
<220> FEATURE:
<221> NAME/KEY: CDS
<222> LOCATION: (1)..(414)

<400> SEQUENCE: 3 atg gga tgg agc tgg atc ttt ctc ttc ctc ctg tca gga act gca ggt      48
Met Gly Trp Ser Trp Ile Phe Leu Phe Leu Leu Ser Gly Thr Ala Gly
1               5                   10                  15 gtc cac tct gag gtc cag ctg caa cag tct gga cct gag ctg gtg aag      96
Val His Ser Glu Val Gln Leu Gln Gln Ser Gly Pro Glu Leu Val Lys
            20                  25                  30 cct gga gct tca atg aag att tcc tgc aag gct tct ggt tac tca ttc     144
Pro Gly Ala Ser Met Lys Ile Ser Cys Lys Ala Ser Gly Tyr Ser Phe
        35                  40                  45 act ggc tac acc atg aac tgg gtg aag cag agc cat gga aag aac ctt     192
Thr Gly Tyr Thr Met Asn Trp Val Lys Gln Ser His Gly Lys Asn Leu
    50                  55                  60 gaa tgg att gga ctt att aat cct cac aat ggt ggt act acc tac aac     240
Glu Trp Ile Gly Leu Ile Asn Pro His Asn Gly Gly Thr Thr Tyr Asn
65                  70                  75                  80 cag aag ttc aag ggc aag gcc aca tta act gta gac aag tca tcc aac     288
Gln Lys Phe Lys Gly Lys Ala Thr Leu Thr Val Asp Lys Ser Ser Asn
                85                  90                  95 aca gcc tac atg gag ctc ctc agt ctg aca tct gag gac tct gca gtc     336
Thr Ala Tyr Met Glu Leu Leu Ser Leu Thr Ser Glu Asp Ser Ala Val
            100                 105                 110 tat tac tgt aca aga ccc ggg ggt tac tac tgg ttc ttc gat gtc tgg     384
Tyr Tyr Cys Thr Arg Pro Gly Gly Tyr Tyr Trp Phe Phe Asp Val Trp
        115                 120                 125 ggc gca ggg acc acg gtc acc gtc tcc tca                             414
Gly Ala Gly Thr Thr Val Thr Val Ser Ser
    130                 135

<210> SEQ ID NO 4
<211> LENGTH: 138
<212> TYPE: PRT
<213> ORGANISM: Mus musculus

<400> SEQUENCE: 4

Met Gly Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Met Asn Trp Val Lys Gln Ser His Gly Lys Asn Leu
    50                  55                  60

Glu Trp Ile Gly Leu Ile Asn Pro His Asn Gly Gly Thr Thr Tyr Asn
65                  70                  75                  80

Gln Lys Phe Lys Gly Lys Ala Thr Leu Thr Val Asp Lys Ser Ser Asn
                85                  90                  95

Thr Ala Tyr Met Glu Leu Leu Ser Leu Thr Ser Glu Asp Ser Ala Val
```

```
                100             105             110
Tyr Tyr Cys Thr Arg Pro Gly Gly Tyr Tyr Trp Phe Phe Asp Val Trp
        115                 120                 125

Gly Ala Gly Thr Thr Val Thr Val Ser Ser
        130                 135

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 5
gggaagatgg atacagttgg tg                                    22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 6
caagagcttc aacaggaatg ag                                    22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 7
atggagttag tttgggcagc ag                                    22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 8
gcacaaccac catactgaga ag                                    22
```